US012788816B2

(12) United States Patent
Kwon et al.

(10) Patent No.: US 12,788,816 B2
(45) **Date of Patent: *Nov. 10, 2026**

(54) CHIMERIC ANTIGEN RECEPTOR WITH 4-IBB COSTIMULATORY DOMAIN

(71) Applicant: EUTILEX CO., LTD., Seoul (KR)

(72) Inventors: Byoung S. Kwon, Seoul (KR); Kwanghee Kim, Seoul (KR); Jiwon Chung, Seoul (KR); Young Gyoon Chang, Seoul (KR); Bo-Rim Yi, Seoul (KR); Jungyun Lee, Seoul (KR); Sae Rom Lee, Seoul (KR); Hyuntae Son, Seoul (KR); Hye Mi Lee, Seoul (KR); Eun Hye Yoo, Seoul (KR)

(73) Assignee: EUTILEX CO., LTD., Seoul (KR)

( * ) Notice: Subject to any disclaimer, the term of this patent is extended or adjusted under 35 U.S.C. 154(b) by 1049 days.

This patent is subject to a terminal disclaimer.

(21) Appl. No.: 17/622,503

(22) PCT Filed: Jun. 26, 2020

(86) PCT No.: PCT/IB2020/056097

§ 371 (c)(1),
(2) Date: Dec. 23, 2021

(87) PCT Pub. No.: WO2020/261231

PCT Pub. Date: Dec. 30, 2020

(65) Prior Publication Data

US 2022/0249565 A1 Aug. 11, 2022

Related U.S. Application Data

(63) Continuation-in-part of application No. 16/715,462, filed on Dec. 16, 2019, now Pat. No. 11,013,765.

(Continued)

(51) Int. Cl.

| | |
|---|---|
| ***A61K 40/31*** | (2025.01) |
| ***A61K 38/00*** | (2006.01) |
| ***A61K 39/00*** | (2006.01) |
| ***A61K 40/11*** | (2025.01) |
| ***A61K 40/42*** | (2025.01) |

(Continued)

(52) U.S. Cl.

CPC .............. *A61K 40/31* (2025.01); *A61K 40/11* (2025.01); *A61K 40/4211* (2025.01); *A61K 40/4261* (2025.01); *A61P 35/00* (2018.01); *C07K 14/7051* (2013.01); *C07K 14/70517* (2013.01); *C07K 14/70578* (2013.01); *C07K 16/2803* (2013.01); *C07K 16/303* (2013.01); *C12N 5/0636* (2013.01); *C12N 5/0646* (2013.01); *C12N 15/86* (2013.01); *A61K 38/00* (2013.01); *A61K 2039/505* (2013.01); *A61K 2239/31* (2023.05); *A61K 2239/38* (2023.05); *C07K 2317/21* (2013.01); *C07K 2317/24* (2013.01); *C07K 2317/622* (2013.01); *C07K 2317/73* (2013.01); *C07K 2319/02* (2013.01); *C07K 2319/03* (2013.01); *C07K 2319/33* (2013.01); *C12N 2740/15043* (2013.01)

(58) Field of Classification Search

CPC .... A61K 40/31; A61K 40/11; A61K 40/4211; A61K 40/4261; A61K 38/00; A61K 2039/505; A61K 2239/31; A61K 2239/38; A61P 35/00; C07K 14/7051; C07K 14/70517; C07K 14/70578; C07K 16/2803; C07K 16/303; C07K 2317/21; C07K 2317/24; C07K 2317/622; C07K 2317/73; C07K 2319/02; C07K 2319/03; C07K 2319/33; C07K 14/70503; C07K 14/70514; C12N 5/0636; C12N 5/0646; C12N 15/86; C12N 2740/15043; C12N 2510/00; C12N 2740/16043

See application file for complete search history.

(56) References Cited

U.S. PATENT DOCUMENTS

| | | | |
|---|---|---|---|
| 7,435,596 | B2 | 10/2008 | Campana et al. |
| 8,026,097 | B2 | 9/2011 | Campana et al. |

(Continued)

FOREIGN PATENT DOCUMENTS

| | | | |
|---|---|---|---|
| CN | 105906720 | A | 8/2016 |
| CN | 108165568 | A | 6/2018 |

(Continued)

OTHER PUBLICATIONS

Zhang C, Liu J, Zhong JF, Zhang X. Engineering CAR-T cells. Biomark Res. Jun. 24, 2017;5:22. doi: 10.1186/s40364-017-0102-y. PMID: 28652918; PMCID: PMC5482931 (Year: 2017).*

(Continued)

*Primary Examiner* — Gregory S Emch
*Assistant Examiner* — Kathleen Cunningchen
(74) *Attorney, Agent, or Firm* — Wood, Phillips, Katz, Clark & Mortimer

(57) ABSTRACT

Provided are CAR-T compositions that are directed to a CAR including (i) an extracellular domain comprising an antigen-binding domain; (ii) a transmembrane domain; and (iii) an intracellular domain comprising a costimulatory endodomain, wherein the costimulatory endodomain comprises an intracellular signaling domain from 4-1BB/CD137 and five additional amino acids. The disclosure also provides vectors, compositions, and methods of treatment using the antigen binding molecules and engineered immune cells comprising the CAR. The CAR compositions provided herein can be used for the treatment of certain cancers.

44 Claims, 15 Drawing Sheets

Specification includes a Sequence Listing.

Related U.S. Application Data

(60) Provisional application No. 63/043,237, filed on Jun. 24, 2020, provisional application No. 63/004,827, filed on Apr. 3, 2020, provisional application No. 62/991,493, filed on Mar. 18, 2020, provisional application No. 62/867,503, filed on Jun. 27, 2019.

(51) Int. Cl.

| | |
|---|---|
| ***A61P 35/00*** | (2006.01) |
| ***C07K 14/705*** | (2006.01) |
| ***C07K 16/28*** | (2006.01) |
| ***C07K 16/30*** | (2006.01) |
| ***C12N 5/0783*** | (2010.01) |
| ***C12N 15/86*** | (2006.01) |

(56) References Cited

U.S. PATENT DOCUMENTS

| | | | | |
|---|---|---|---|---|
| 8,399,645 | B2 | 3/2013 | Campana et al. | |
| 9,605,049 | B2 | 3/2017 | Campana et al. | |
| 9,834,590 | B2 | 12/2017 | Campana et al. | |
| 9,856,322 | B2 | 1/2018 | Campana et al. | |
| 10,150,816 | B2 | 12/2018 | Abbot et al. | |
| 10,195,272 | B2 | 2/2019 | Ma | |
| 10,421,810 | B2 | 9/2019 | Orentas et al. | |
| 10,442,867 | B2 | 10/2019 | Orentas et al. | |
| 2005/0113564 | A1 | 5/2005 | Campana et al. | |
| 2006/0093605 | A1 | 5/2006 | Campana et al. | |
| 2009/0011498 | A1 | 1/2009 | Campana et al. | |
| 2012/0015434 | A1 | 1/2012 | Campana et al. | |
| 2012/0282256 | A1 | 11/2012 | Campana et al. | |
| 2013/0216509 | A1 | 8/2013 | Campana et al. | |
| 2013/0266551 | A1 | 10/2013 | Campana et al. | |
| 2014/0328812 | A1 | 11/2014 | Campana et al. | |
| 2014/0341869 | A1 | 11/2014 | Campana et al. | |
| 2015/0307623 | A1 | 10/2015 | Abbot et al. | |
| 2016/0009784 | A1 | 1/2016 | Campana et al. | |
| 2016/0053017 | A1 | 2/2016 | Orentas et al. | |
| 2016/0355590 | A1 | 12/2016 | Epstein | |
| 2017/0283482 | A1 | 10/2017 | Campana et al. | |
| 2018/0057563 | A1 | 3/2018 | Campana et al. | |
| 2018/0118845 | A1 | 5/2018 | Campana et al. | |
| 2018/0193452 | A1 | 7/2018 | Ma | |
| 2018/0305452 | A1* | 10/2018 | Orentas | A61K 40/11 |
| 2018/0355052 | A1 | 12/2018 | Orentas et al. | |
| 2019/0091308 | A1* | 3/2019 | Low | A61K 48/005 |
| 2019/0119399 | A1 | 4/2019 | Abbot et al. | |
| 2019/0151362 | A1* | 5/2019 | Li | A61K 40/31 |
| 2019/0202913 | A1* | 7/2019 | Kochenderfer | C07K 14/70578 |
| 2020/0079849 | A1 | 3/2020 | Orentas et al. | |
| 2020/0109210 | A1 | 4/2020 | Orentas et al. | |
| 2022/0195397 | A1* | 6/2022 | Liao | A61K 40/4261 |

FOREIGN PATENT DOCUMENTS

| | | | |
|---|---|---|---|
| CN | 108728459 | A | 11/2018 |
| WO | WO 2005/044996 | A2 | 5/2005 |
| WO | 2015069922 | A2 | 5/2015 |
| WO | WO 2017/062820 | A1 | 4/2017 |
| WO | 2018106993 | A1 | 6/2018 |
| WO | 2018132513 | A1 | 7/2018 |
| WO | 2018156711 | A1 | 8/2018 |

OTHER PUBLICATIONS

Chiu ML et al. Antibodies Aug. 2019, 55, 1-80 (Year: 2019).*

Uniprot Q07011 "TNR9_HUMAN" (Year: 2025).*

Almagro et. al., Front. Immunol. Aug. 2018:175 (Year: 2018).*

Yang, et. al. A Simplified Method for the Clinical-scale Generation of Central Memory-like CD8+ T Cells After Transduction With Lentiviral Vectors Encoding Antitumor Antigen T-cell Receptors. Journal of Immunotherapy 33(6):p. 648-658, Jul. 2010. DOI: 10.1097/CJI.0b013e3181e311cb (Year: 2010).*

Expasy Translate tool—translation of SEQ ID No. 2 (Year: 2025).*

Kügler M, et. al. Stabilization and humanization of a single-chain Fv antibody fragment specific for human lymphocyte antigen CD19 by designed point mutations and CDR-grafting onto a human framework. Protein Eng Des Sel. Mar. 2009;22(3): 135-47. doi: 10.1093/protein/gzn079. Epub Feb. 1, 2009. (Year: 2009).*

Martyniszyn A, Krahl AC, Andre MC, Hombach AA, Abken H. CD20-CD19 Bispecific CAR T Cells for the Treatment of B-Cell Malignancies. Hum Gene Ther. Dec. 2017;28(12):1147-1157. doi: 10.1089/hum.2017.126. PMID: 29207878 published Dec. 1, 2017 (Year: 2017).*

Cho, J.H., Collins, J.J. and Wong, W.W., 2018. Universal chimeric antigen receptors for multiplexed and logical control of T cell responses. Cell, 173(6), pp. 1426-1438 (Year: 2018).*

Nakano K, Ishiguro T, Konishi H, Tanaka M, Sugimoto M, Sugo I, et al Generation of a humanized anti-glypican 3 antibody by CDR grafting and stability optimization. Anticancer Drugs 2010;21:907-16 (Abstract) (Year: 2010).*

Nelson, A.L., Dhimolea, E. and Reichert, J.M., 2010. Development trends for human monoclonal antibody therapeutics. Nature reviews drug discovery, 9(10), pp. 767-774 (Year: 2010).*

Li, J., Li, W., Huang, K et al. Chimeric antigen receptor T cell (CAR-T) immunotherapy for solid tumors: lessons learned and strategies for moving forward. J Hematol Oncol 11, 22 (2018). https://doi.org/10.1186/s13045-018-0568-6 (Year: 2018).*

Chen C, et. al. Development of T cells carrying two complementary chimeric antigen receptors against glypican-3 and asialoglycoprotein receptor 1 for the treatment of hepatocellular carcinoma. Cancer Immunol Immunother. Apr. 2017;66(4):475-489. doi: 10.1007/s00262-016-1949-8. Epub Dec. 29, 2016. (Year: 2016).*

Zah et. al.; T Cells Expressing CD19/CD20 Bispecific Chimeric Antigen Receptors Prevent Antigen Escape by Malignant B Cells. Cancer Immunol Res Jun. 1, 2016; 4 (6): 498-508. https://doi.org/10.1158/2326-6066.CIR-15-0231 (Year: 2016).*

International Search Report and Written Opinion issued Sep. 24, 2020 in PCT/IB2020/056097 filed Jun. 26, 2020, 12 pages.

GenBank, "Human receptor protein 4-1BB mRNA, complete cds", NCBI, 1994, 2 total pages.

* cited by examiner

CHIMERIC ANTIGEN RECEPTOR WITH 4-IBB COSTIMULATORY DOMAIN

CROSS-REFERENCE TO RELATED APPLICATION

This application is a National Stage (371) of PCT/IB2020/056097, filed on Jun. 26, 2020, which claims priority to: U.S. 63/043,237, filed Jun. 24, 2020, U.S. 63/004,827, Apr. 3, 2020, U.S. 62/991,493, filed Mar. 18, 2020, U.S. Ser. No. 16/715,462, filed Dec. 16, 2019, PCT/KR2019/010244, filed Aug. 12, 2019, and U.S. 62/867,503, filed Jun. 27, 2019.

BACKGROUND

Cancer remains one of the leading causes of death in the world. Recent statistics report that 13% of the world population dies from cancer. According to estimates from the International Agency for Research on Cancer (IARC), in 2012 there were 14.1 million new cancer cases and 8.2 million cancer deaths worldwide. By 2030, the global burden is expected to grow to 21.7 million new cancer cases and 13 million cancer deaths due to population growth and aging and exposure to risk factors such as smoking, unhealthy diet and physical inactivity. Further, pain and medical expenses for cancer treatment cause reduced quality of life for both cancer patients and their families.

T cells engineered with chimeric antigen receptors (CAR-T) have great therapeutic potential for treating diseases such as cancers. CAR-T therapeutics confer powerful target affinity and signaling function on T cell. However, the impressive efficacy of CAR-T therapies is frequently accompanied by severe side effects, such as cytokine release syndrome (CRS). Thus, there remains an unmet need to develop CAR-T therapeutics and strategies that have reduced side effects.

SUMMARY

Provided herein are immune cells comprising a chimeric antigen receptor (CAR), wherein the (CAR) comprises: (a) an extracellular domain comprising an antigen-binding domain; (b) a transmembrane domain; and (c) an intracellular domain comprising a costimulatory endodomain, wherein the costimulatory endodomain comprises an intracellular signaling domain from 4-1BB/CD137 and five additional amino acids.

In some embodiments, the chimeric antigen receptor is a single polypeptide. In some embodiments, the chimeric antigen receptor is comprised of two polypeptides.

In some embodiments, the costimulatory endodomain comprises an intracellular signaling domain from 4-1BB/CD137 and five additional amino acids, wherein the five additional amino acids are encoded by SEQ ID NO: 1. In some embodiments, the costimulatory endodomain comprises SEQ ID NO: 2.

In some embodiments, the antigen-binding domain is humanized. In some embodiments, the antigen-binding domain is human. In some embodiments, the antigen-binding domain is an scFv. In some embodiments, the antigen-binding domain specifically binds an antigen associated with a disease. In some embodiments, the antigen-binding domain specifically binds a tumor antigen. In some embodiments, the antigen-binding domain specifically binds to an antigen selected from the group consisting of: glypican-3 (GPC3), malignancy variant receptor (MVR), and CD19.

In some embodiments, the transmembrane domain is a transmembrane domain selected from a protein selected from the group consisting of: 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD84, CD8, CD8 alpha, CD8 beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), an integrin, ITGA4, ITGA6, ITGAD, ITGAE, ITGAL, ITGAM, ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1), an MEC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecule (a SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6. In some embodiments, the transmembrane domain is a transmembrane domain from CD8α. In some embodiments, the intracellular domain further comprises an intracellular domain from CD3ζ.

In some embodiments, the chimeric antigen receptor further comprises a signal peptide or leader sequence. In some embodiments, the chimeric antigen receptor further comprises a hinge region. In some embodiments, the hinge region is a CD8α hinge. In some embodiments, the chimeric antigen receptor further comprises an additional antigen-binding domain. In some embodiments, the additional antigen-binding domain is an scFv.

In some embodiments, the immune cell is a human immune cell. In some embodiments, the human immune cell is an autologous human immune cell. In some embodiments, the human immune cell is an allogenic human immune cell. In some embodiments, the immune cell is a T cell. In some embodiments, the immune cell is an NK cell.

Provided herein are nucleic acids encoding a chimeric antigen receptor (CAR), wherein the chimeric antigen receptor comprises: (a) an extracellular domain comprising an antigen-binding domain; (b) a transmembrane domain; and (c) an intracellular domain comprising a costimulatory endodomain, wherein the costimulatory endodomain comprises an intracellular signaling domain from 4-1BB/CD137 and five additional amino acids.

In some embodiments, the chimeric antigen receptor is a single polypeptide. In some embodiments, the chimeric antigen receptor is comprised of two polypeptides.

In some embodiments, the costimulatory endodomain comprises an intracellular signaling domain from 4-1BB/CD137 and five additional amino acids, wherein the five additional amino acids are encoded by a nucleotide sequence of SEQ ID NO: 1. In some embodiments, the costimulatory endodomain comprises SEQ ID NO: 2.

In some embodiments, the antigen-binding domain is humanized. In some embodiments, the antigen-binding domain is human. In some embodiments, the antigen-binding domain is an scFv. In some embodiments, the antigen-binding domain specifically binds an antigen associated with a disease. In some embodiments, the antigen-binding domain specifically binds a tumor antigen. In some embodiments, the antigen-binding domain specifically binds to an antigen selected from the group consisting of: glycan-3 (GPC3), malignancy variant receptor (MVR), and CD19.

In some embodiments, the transmembrane domain is a transmembrane domain selected from a protein selected from the group consisting of: 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD84, CD8, CD8 alpha, CD8 beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), an integrin, ITGA4, ITGA6, ITGAD, ITGAE, ITGAL, ITGAM, ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1), an MEC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecule (a SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6. In some embodiments, the transmembrane domain is a transmembrane domain from CD8 alpha.

In some embodiments, the intracellular domain further comprises an intracellular domain from CD3ζ. In some embodiments, the chimeric antigen receptor further comprises a signal peptide or leader sequence. In some embodiments, the chimeric antigen receptor further comprises a hinge region. In some embodiments, the hinge region is a CD8α hinge.

Provided herein are vectors comprising any one of the nucleic acids described herein. In some embodiments, the vector further comprises a promoter operationally linked to the nucleic acid. In some embodiments, the promoter is a constitutive promoter. In some embodiments, the promoter is an inducible promoter. In some embodiments, the vector is a viral vector. In some embodiments, the viral vector is a lentiviral vector.

Provided herein are methods of producing an engineered immune cell, the method comprising: introducing into an immune cell any one of the nucleic acids described herein or any one of the vectors described herein, thereby producing the engineered immune cell. In some embodiments, the method further comprises, after the introducing step, culturing the engineered immune cell. In some embodiments, the immune cell is a T cell. In some embodiments, the immune cell is a NK cell.

In some embodiments, the method further comprises, before the introducing step, obtaining the immune cell from a subject. In some embodiments, the method further comprises administering the engineered immune cell to the subject. In some embodiments, the subject has been diagnosed or identified as having a cancer.

Provided herein are engineered immune cells produced by any one of the methods described herein.

Provided herein are pharmaceutical compositions comprising any one of the engineered immune cells described herein and a pharmaceutically acceptable carrier.

Provided herein are methods of treating a cancer in a subject, the method comprising administering to the subject any one of the engineered immune cells described herein or any one of the pharmaceutical compositions described herein. In some embodiments, the cancer is an anti-glypican-3-associated cancer, an anti-CD19-associated cancer, or an anti-MVR-associated cancer. In some embodiments, the cancer is carcinoma, lymphoma (e.g., Hodgkin's and non-Hodgkin's lymphomas), blastoma, sarcoma, leukemia, squamous cell carcinoma, small cell lung cancer, non-small cell lung cancer, lung adenocarcinoma, squamous cell carcinoma of the lung, peritoneal cancer, hepatocellular carcinoma, gastric cancer, pancreatic cancer, glioma, cervical cancer, ovarian cancer, liver cancer, bladder cancer, breast cancer, colon cancer, colorectal cancer, endometrial or uterine carcinoma, salivary carcinoma, kidney cancer, prostate cancer, vulvar cancer, thyroid cancer, liver carcinoma, other lymphoproliferative disorders, and various types of head and neck cancer. In some embodiments, the subject has previously been administered one or more additional anticancer therapies selected from the group consisting of: ionizing radiation, a chemotherapeutic agent, a therapeutic antibody, and a checkpoint inhibitor. In some embodiments, the subject has been identified or diagnosed as having the cancer.

DETAILED DESCRIPTION

Figure 1:
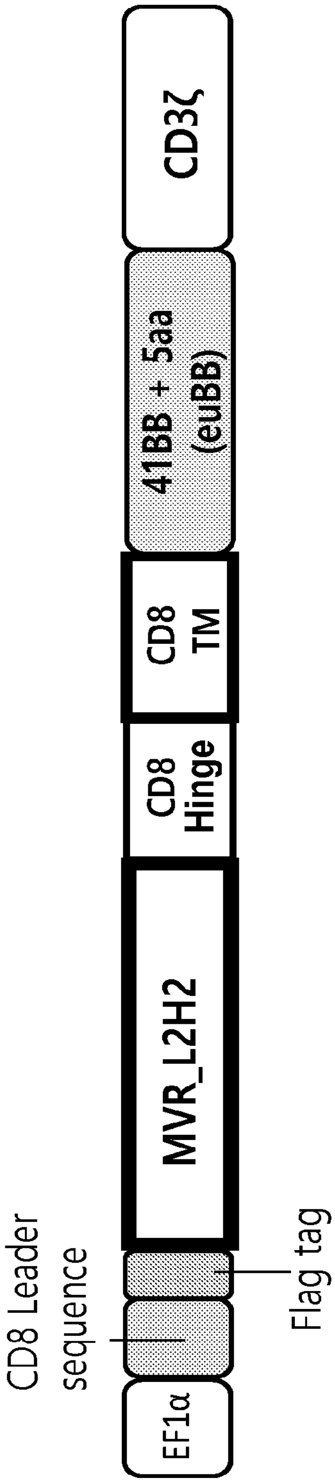
FIG. 1 shows a schematic of an exemplary MVR CAR construct.

This disclosure describes chimeric antigen receptors (CARs) that include a 4-1BB costimulatory endodomain, as well as methods of making and using the same.

Definitions

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that are within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc. In some embodiments, administration may involve a single dose, multiple doses, or a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the strength a particular ligand binds to its partner. Affinity can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Antibody agent: As used herein, the term "antibody agent" can refer to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies, polyclonal antibodies, and fragments thereof. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, in some embodiments, an antibody agent utilized in accordance with the present invention is in a format selected from, but not limited to, intact IgA, IgG, IgE, or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody agent may lack a covalent modification (e.g., attachment of a glycan) that it would have if produced naturally. In some embodiments, an antibody agent may contain a covalent modification (e.g., attachment of a glycan, a payload [e.g., a detectable moiety, a therapeutic moiety, a catalytic moiety, etc.], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR). In some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments, an included CDR is substantially identical to a reference CDR in that it is either identical in sequence or contains between 1-5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain. In some embodiments, an antibody agent is or comprises at least a portion of a chimeric antigen receptor (CAR).

Antigen: The term "antigen", as used herein, can refer to an agent that binds to an antibody agent. In some embodiments, an antigen binds to an antibody agent and may or may not induce a particular physiological response in an organism. In general, an antigen may be or include any chemical entity such as, for example, a small molecule, a nucleic acid, a polypeptide, a carbohydrate, a lipid, a polymer (including biologic polymers [e.g., nucleic acid and/or amino acid polymers] and polymers other than biologic polymers [e.g., other than a nucleic acid or amino acid polymer]), etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some certain embodiments, an antigen is present in a cellular context (e.g., an antigen is expressed on the surface of a cell or expressed in a cell). In some embodiments, an antigen is a recombinant antigen.

Antigen binding domain: The term "antigen binding domain", as used herein, can refer to an antibody agent or portion thereof that specifically binds to a target moiety or entity. Typically, the interaction between an antigen binding domain and its target is non-covalent. In some embodiments, a target moiety or entity can be of any chemical class including, for example, a carbohydrate, a lipid, a nucleic acid, a metal, a polypeptide, or a small molecule. In some embodiments, an antigen binding domain may be or comprise a polypeptide (or complex thereof). In some embodiments, an antigen binding domain is part of a fusion polypeptide. In some embodiments, an antigen binding domain is part of a chimeric antigen receptor (CAR).

Associated with: Two events or entities are "associated" with one another, as that term is used herein, if the presence, level, and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another. In some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties. Indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

CDR: As used herein, "CDR", can refer to a complementarity determining region within a variable region of an antibody agent. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

Chemotherapeutic Agent: The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more *vinca* alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine.

Engineered: In general, the term "engineered" can refer to the aspect of having been manipulated by the hand of man. For example, a polypeptide is considered to be "engineered" when the polypeptide sequence manipulated by the hand of man. For example, in some embodiments of the present invention, an engineered polypeptide comprises a sequence that includes one or more amino acid mutations, deletions and/or insertions that have been introduced by the hand of man into a reference polypeptide sequence. In some embodiments, an engineered polypeptide includes a polypeptide that has been fused (i.e., covalently linked) to one or more additional polypeptides by the hand of man, to form a fusion polypeptide that would not naturally occur in vivo. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, derivatives and/or progeny of an engineered polypeptide or cell are typically still referred to as "engineered" even though the actual manipulation was performed on a prior entity.

Host cell: The term "host cell", as used herein, can refer to a cell of an organism that is selected, modified, transformed, grown, use or manipulated in any way, for the production of material by the cell, for example the expression by the cell of a gene, a DNA or RNA sequence, a protein or an enzyme. Host cells can include immune cells, including but not limited to lymphocytes (e.g., T cells, B cells, and NK cells), neutrophils, and monocytes/macrophages.

In vitro: The term "in vitro", as used herein, refers to events that occur in an artificial environment, e.g., in a test tube or reaction vessel, in cell culture, etc., rather than within a multi-cellular organism.

In vivo: The term "in vivo" as used herein refers to events that occur within a multi-cellular organism, such as a human and a non-human animal. In the context of cell-based systems, the term may be used to refer to events that occur within a living cell (as opposed to, for example, in vitro systems).

Isolated: The term "isolated" as used herein, can refer to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Operably linked: The term "operably linked" as used herein, can refer to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest. In some embodiments, control elements act in trans to or otherwise at a from the functional element of interest.

Pharmaceutical composition: As used herein, the term "pharmaceutical composition" refers to a composition in which an active agent is formulated together with one or more pharmaceutically acceptable carriers. In some embodiments, the composition is suitable for administration to a human or animal subject. In some embodiments, the active agent is present in unit dose amount appropriate for administration in a therapeutic regimen that shows a statistically significant probability of achieving a predetermined therapeutic effect when administered to a relevant population.

Polypeptide: The term "polypeptide", as used herein, generally refers to its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibody agents, antibody fragments, biologically active portions thereof, and/or characteristic portions thereof.

Prevent or prevention: The terms "prevent" or "prevention", as used herein, when used in connection with the occurrence of a disease, disorder, and/or condition, can refer to reducing the risk of developing the disease, disorder and/or condition and/or to delaying onset and/or severity of one or more characteristics or symptoms of the disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder, or condition is observed in a population susceptible to the disease, disorder, or condition.

Recombinant: The term "recombinant", as used herein, can refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that are transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Specific binding: As used herein, the term "specific binding" can refer to an ability to discriminate between possible binding partners in the environment in which binding can occur. A binding agent that interacts with one particular target when other potential targets are present is said to "bind specifically" to the target with which it interacts. In some embodiments, specific binding is assessed by detecting or determining degree of association between the binding agent and its partner. In some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically Effective Amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy, such as a pancreatic carcinoma, or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Transfection: The term "transfection", as used herein, can refer to the introduction of a foreign nucleic acid into a cell using recombinant DNA technology. The term "transformation" as used herein can refer to the introduction of a foreign gene, DNA, or RNA sequence to a host cell, so that the host cell will express the introduced gene or sequence to produce the encoded protein or enzyme.

Transduction: The term "transduction", as used herein, can refer to the introduction of a foreign nucleic acid into a cell using a viral vector.

Variant: As used herein in the context of molecules, e.g., nucleic acids, proteins, or small molecules, the term "variant" can refer to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence. In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid.

Vector: The term "vector", as used herein, can refer to a nucleic acid molecule capable of transporting another nucleic acid to which it has been linked. Vectors can encompass both non-viral and viral carriers for introducing nucleic acids into cells in vitro, ex vivo, or in vivo.

A vector may be a replicon with another DNA fragment attached to amplify the attached fragment. The term "replicon" refers to any genetic element (e.g., a plasmid, phage, cosmid, chromosome, or virus) that is able to act as an autonomous unit of in vivo DNA replication. Many vectors known in the art may be used to engineer nucleic acids, incorporate response elements and promoters into genes, and the like. Preferred vectors include, but are not limited to, plasmids (e.g., PBR322 or pUC plasmid derivatives), modified viruses (e.g., adenoviruses, retroviruses, adeno-associated viruses, or herpes viruses), or Bluescript vectors. For example, DNA fragments corresponding to reaction elements and promoters may be inserted into appropriate vectors by combining the appropriate DNA fragments with selected vectors having complementary cohesive termini. In some embodiments, the termini of the DNA molecules may be enzymatically modified, or any site may be generated by binding the nucleotide sequence with the DNA ends via a linker. In some embodiments, vectors may be manipulated to contain a selection marker gene for screening cells that have incorporated the marker into the cell genome. Such markers make it possible to identify and/or screen host cells expressing the protein encoded by the marker.

One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Non-limiting examples of expression vectors and packaging constructs that can be used to deliver the chimeric antigen receptors described herein include retroviral vectors (e.g., SFG, pMX, pSAMEN, pMP71, pLXSN, pMSCV, pMSGV), lentiviral vectors (e.g., epHIV7, pLenO, pSIN, pSIEW, pELPS, pELNS, pHR), packaging constructs (psPAX2, pRDF, pEQ-PAM3(-E), pVSVg, pCL, pMEVSVg, pMD2G, pMDLg/p.RRE, pRSV.REV, pTSV.rev, pCHGP, pCMV-g, pCMV-Rev2, pCMVdR8.91, pGALV).

In some embodiments, a vector provides the necessary regulatory sequences (e.g., transcriptional and translational elements) to regulate the expression of the fusion protein in the appropriate host cell. Regulatory sequences may comprise promoter regions, enhancer regions, transcription termination sites, ribosomal binding sites, initiation codons, splice signals, introns, polyadenylation signals, Shine/Dalgarno translation sequences and Kozak consensus sequences. A regulatory sequence is selected in view of the host cell in which the fusion protein will be produced. In some embodiments, suitable bacterial promoters include, but are not limited to, bacteriophage λpL or pR, T6, T7, T7/lacO, lac, recA, gal, trp, ara, hut and trp-lac. In some embodiments, suitable eukaryotic promoters include, but are not limited to, PRBI, GAPDH, metallothionein, thymidine kinase, viral LTR, cytomegalovirus, SV40, or tissue-specific or tumor-specific promoters such as α-fetal protein, amylase, cathepsin E, M1 muscarinic receptor or γ-glutamyl transferase.

In some embodiments, additional vectors include lipoplexes (cationic liposome-DNA complexes), polyplexes (cationic polymer-DNA complexes) and protein-DNA complexes. In addition to nucleic acids, the vector may also comprise one or more regulatory regions and/or selectable markers useful for selecting, measuring, and monitoring the outcomes of nucleic acid delivery (e.g., delivery to a certain tissue, or duration of expression).

Vectors may be introduced into a desired host cell by methods known in the art, such as injection, transfection, electroporation, microinjection, transduction, cell fusion, lipofection, calcium phosphate precipitation (Graham, F. L. et al., Virology, 52: 456 (1973), Chen and Okayama, Mol. Cell. Biol. 7: 2745-2752 (1987)), liposome-mediated textured salt method (Wong, T. K. et al., Gene, 10:87 (1980), Nicolau and Sene, Biochim. Biophys.Acta, 721: 185-190 (1982), Nicolau et al., Methods Enzymol., 149: 157-176 (1987)), DEAE-dextran treatment (Gopal, Mol. Cell Biol., 5: 1188-1190 (1985)), gene bombardment (Yang et al., Proc. Natl. Acad. Sci., 87: 9568-9572 (1990)) using gene species or DNA vector transporters (see Wu et al., J. Biol. Chem. 267: 963 (1992), Wu et al., J. Biol. Chem. 263: 14621 (1988), Hartmut et al., Canadian Patent Application No. 2,012,311).

In some embodiments, viral vectors have been used in a wide range of gene transfer applications in cells as well as in live animal subjects. Viral vectors that may be used include, but are not limited to, adenovirus, retrovirus, vaccinia virus, poxvirus, adeno-associated virus, herpes simplex virus, lentivirus, baculovirus, sendai virus, measles virus, simian virus 40, and Epstein-Barr virus vectors. Non-viral vectors include plasmids, lipoplexes (cationic liposome-DNA complexes), polyplexes (cationic polymer-DNA complexes) and protein-DNA complexes. In addition to nucleic acids, the vector may comprise one or more regulatory regions and/or selection markers useful for screening, measuring, and monitoring nucleic acid delivery outcomes (e.g., delivery to tissue, or persistence of expression).

In some embodiments, polynucleotides may be introduced in vivo by lipofection. The use of liposomes for encapsulating and transfecting nucleic acids in vitro has increased. In some embodiments, synthetic cationic lipids, designed to limit the difficulties and risks encountered by liposome-mediated transfection may be used to prepare liposomes for in vivo transfection of genes (Feigner et al., Proc. Natl. Acad. Sci. USA. 84:7413 (1987), Mackey et al., Proc. Natl. Acad. Sci. USA 85:8027 (1988), Ulmer et al., Science 259:1745 (1993)). In some embodiments, the use of cationic lipids may promote encapsulation of negatively charged nucleic acids and may also promote fusion with negatively charged cell membranes (Feigner et al., Science 337:387 (1989)). Particularly useful lipid compounds and compositions for the delivery of nucleic acids are described in WO95/18863, WO96/17823, and U.S. Pat. No. 5,459,127, which are herein incorporated by reference in their entirety. In some embodiments, direct transfection to specific cell types will clearly be particularly desirable for tissues with cellular heterogeneity such as the pancreas, liver, kidney and brain. In some embodiments, lipids may chemically bind to other molecules for targeting (Mackey et al., 1988). In some embodiments, targeted peptides such as hormones or neurotransmitters, and proteins such as antibodies, or non-peptidic molecules may be chemically bound to liposomes.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual* 2$^{nd}$ ed., Cold Spring Harbor Laboratory Press, Cold Spring Harbor, N.Y. (1989)), which is incorporated herein by reference for any purpose.

Engineered Immune Cells

As used herein, "immune cells" refer to cells of the immune system which can be categorized as lymphocytes (e.g., T cells, B cells, and NK cells), neutrophils, and monocytes/macrophages. In some embodiments, the immune cell is a T cell. In some embodiments, the immune cell is an NK cell. In some embodiments, the immune cell is a Macrophage. In some embodiments, an immune cell is an engineered immune cell, meaning the immune cell has been genetically modified to express a non-naturally occurring protein (e.g., a chimeric antigen receptor) or to include an exogenous nucleic acid.

The immune cells (e.g., T cells) may be modified in one or more than one manner. Immune cells (e.g., T cells) may express at least one non-natural molecule that is a receptor for an antigen that is present on the surface of one or more types of cells. In some embodiments, immune cells, include immune cells (e.g., T cells) that are not found in nature because they are engineered to comprise or express at least one synthetic molecule that is not found in nature. In specific embodiments, the immune cells (e.g., T cells) are engineered to express at least one chimeric antigen receptor (CAR), including a CAR that targets a specific tumor antigen, such as glypican-3 (GPC3), malignancy variant receptor (MVR), HLA-DR (Human Leukocyte Antigen-D Related), or CD19. In specific embodiments, the immune cell can be a T cell, e.g., a CD4$^{+}$ T cell, a CD8$^{+}$ T cell, a Treg cell, a Th1 T cell, a Th2 T cell, a Th17 T cell, an unspecific T cell, or a population of T cells that comprises a combination of any of the foregoing. Immune cells (e.g., T cells) engineered with chimeric antigen receptors (CAR T cells) have great therapeutic potential for treating cancers. With a CAR, a receptor can be programmed to recognize an antigen, which when bound, activate immune cells to kill the cell expressing that antigen. Therefore, immune cells expressing CAR(s) for an antigen expressed on a tumor cell can target and kill the tumor cell. For example, recent clinical trials of a CD19-targeted CAR-transduced T cell (CD19-CAR T cell) against hematologic malignancies showed a strong effect of CAR T technology. (Kochenderfer, J. N. et al. (2010) *Blood* 116: 4099-4102; Porter, D. L., et al. (2011) *N Engl. J. Med.* 365: 725-733; Grupp, S. A. et al. (2013) *N. Engl. J. Med.* 368: 1509-1518; Kochenderfer, J. N. et al. (2015) *J. Clin. Oncol.* 33: 540-549; Brown, C. E. et al. (2016) *N Engl. J. Med.* 375: 2561-2569). The clinical success of CAR T is attributed, at least in part, to the fusion structure of the CAR, which is made by artificially combining a high-affinity antigen-binding domain with multiple signaling domains (Maus, M. V. et al. (2014) *Blood* 123: 2625-2635; van der Stegen, S. J. et al. (2015) *Nat. Rev. Drug Discov.* 14: 499-509).

CARs comprise an extracellular antigen-binding domain, a transmembrane domain, and an intracellular signaling domain. In some embodiments, the extracellular antigen-binding domain comprises a single chain variable fragment (scFv) that is capable of recognizing a tumor-associated antigen, the transmembrane domain employs the transmembrane domain from molecules such as CD8 and CD28, and the intracellular signaling domain employs an immunoreceptor tyrosine-based activation motif (e.g., CD3ζ) and the intracellular signaling domain of co-stimulatory signaling molecule (e.g., CD28 and CD137 (4-1BB)).

As used herein, "single chain variable fragment, scFv" refers to a fragment of antibody defined as a recombinant protein comprising a heavy chain variable domain (VH) and a light chain variable domain (VL) connected by a linker, which brings the two domains together into association such that an antigen-binding site is formed.

In some embodiments, the transmembrane domain is a transmembrane domain from a protein selected from 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD84, CD8, CD8 alpha, CD8 beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell co-stimulator (ICOS), an integrin, ITGA4, ITGA6, ITGAD, ITGAE, ITGAL, ITGAM, ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1), an MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecule (a SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6.

In some embodiments, the intracellular signaling domain comprises an intracellular signaling domain from a protein selected from 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3delta, CD3epsilon, CD3gamma, CD3zeta, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAM1, CRTAM, a cytokine receptor, DAP-10, DNAM1 (CD226), Fc gamma receptor, GADS, GITR, HVEM (LIGHTR), IA4, ICAM-1, Ig alpha (CD79a), IL-2Rbeta, IL-2R gamma, IL-7R alpha, inducible T cell co-stimulator (ICOS), an integrin, ITGA4, ITGA6, ITGAD, ITGAE, ITGAL, ITGAM, ITGAX, ITGB2, ITGB7, ITGB1, KIRDS2, LAT, ligand that specifically binds with CD83, LIGHT, LTBR, Ly9 (CD229), Ly108, lymphocyte function-associated antigen-1(LFA-1), a MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecules (SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6, or any combination thereof.

In some embodiments, the chimeric antigen receptor further comprises an additional antigen-binding domain. In some embodiments, the chimeric antigen receptor is a bi-specific CAR (i.e., targeting two antigen binding domains). In some embodiments, the chimeric antigen receptor is multivalent (i.e., targeting multiple antigen binding domains). In some embodiments, the additional antigen-binding domain is a scFv.

The immune cells, (e.g., T cells) can come from any source known in the art. For example, immune (e.g., T) cells can be differentiated in vitro from a hematopoietic stem cell population, or immune (e.g., T) cells can be obtained from a subject. T cells can be obtained from peripheral blood mononuclear cells (PBMCs), bone marrow, lymph node tissue, cord blood, thymus tissue, tissue from a site of infection, ascites, pleural effusion, spleen tissue, or tumors. In addition, immune (e.g., T) cells can be derived from one or more immune cell lines available in the art. In some embodiments, T cells can be obtained from blood collected from a subject using any number of techniques known to the skilled artisan, such as FICOLL™ separation and/or apheresis. Additional methods of isolating T cells for a T cell therapy are disclosed in U.S. Patent Publication No. 2013/0287748. Other non-limiting examples can be found in International Application No. PCT/US2015/014520 (published as WO2015/120096) and in International Application No. PCT/US2016/057983 (published as WO2017/070395), each of which is herein incorporated by reference in its entirety.

In some embodiments, the immune cells are autologous T cells. In some embodiments, the immune cells are obtained from a subject that is not the patient. In some embodiments, T cells for using in a therapeutic method are syngeneic (the donor and the recipients are different but are identical twins). In some embodiments, T cells for using in a therapeutic method are allogenic (from the same species but different donor) as the recipient subject. In some embodiments, the T cells are autologous stem cells (for autologous stem cell therapy or ASCT). In some embodiments, the immune cells are non-autologous T-cells. In some embodiments, the immune cells are obtained from a healthy donor. In some embodiments, the immune cells are obtained from a patient afflicted with a cancer or a tumor.

T cells can be engineered to express, for example, chimeric antigen receptors (CARs). In some embodiments, CAR-T cells can be engineered to express an extracellular single chain variable fragment (scFv). In some embodiments, the CAR is engineered such that the costimulatory domain is expressed as a separate polypeptide chain. Exemplary CAR-T cell therapies and constructs are described in U.S. Patent Publication Nos. 2013/0287748, 2014/0227237, 2014/0099309, and 2014/0050708, which are herein incorporated by reference in their entirety.

CAR Construct

The present disclosure provides, at least in part, chimeric antigen receptor (CAR) polypeptides. As used herein, "chimeric antigen receptor (CAR)" refers to a receptor not present in nature and is capable of providing an immune effector cell with a specificity to a particular antigen. In some embodiments, a CAR refers to a receptor used for delivering the specificity of a monoclonal antibody agent to a T cell. Generally, a CAR comprises an extracellular binding domain (ectodomain), a transmembrane domain, and an intracellular signaling domain (endodomain).

In some embodiments, in order to achieve robust immune (e.g., CAR-T) cell expansion, function, persistence and antitumor activity, costimulatory signals can be provided by incorporating intracellular signaling domains from immune (e.g., T cell) cell costimulatory molecules into the CAR construct. In some embodiments, the selection and positioning of co-stimulatory domains within a CAR construct can influence immune (e.g., CAR-T) cell function and fate, and have differential impacts on immune (e.g., CAR-T) cell kinetics, cytotoxic function and potentially safety profile. Non-limiting examples of costimulatory molecules include CD28, ICOS, CD27, 4-1BB/CD137, OX40, and CD40L.

As used herein, 4-1BB/CD137 is an activation-induced T cell costimulatory molecule, expressed on a subset of resting CD8+ T cells and is upregulated on both CD4+ and CD8+ T cells following activation. In some embodiments, T cells expressing CARs that incorporate 4-1BB/CD137 domains can express granzyme B, IFN-γ, TNF-α, GM-CSF and the anti-apoptotic protein Bcl-XL (Zhong et al., Mol. Ther. 2010; 18: 413-420), wherein CARs incorporating a 4-1BB/CD137 costimulatory domain can show longer CAR-T cell persistence (Zhao et al., Cancer Cell 2015; 28: 415-428). In some embodiments, intracellular domain of the chimeric receptors described herein include a 4-1BB signaling domain followed by a five amino acid sequence, which may be further combined with any other desired extracellular, transmembrane, and/or intracellular domain(s) useful in the context of the chimeric receptor.

In some embodiments, a CAR includes: (a) extracellular domain comprising an antigen-binding domain; (b) a transmembrane domain; and (c) an intracellular domain comprising a costimulatory endodomain, wherein the costimulatory endodomain comprises an intracellular signaling domain from 4-1BB/CD137 and five additional amino acids. As contemplated herein, the CAR construct can include an extracellular domain directed to any desired antigen-binding domain. In some embodiments, the costimulatory endodomain includes an intracellular signaling domain from 4-1BB/CD137 and five additional amino acids, wherein the five additional amino acids are encoded by SEQ ID NO: 1. In some embodiments, the costimulatory endodomain comprises SEQ ID NO: 2. In some embodiments, the co-stimulatory endodomain includes a sequence that is at least 80%, 85%, 90%, 91%, 92%, 93%, 94%, 95%, 96%, 97%, 98%, 99%, or 100% identical to SEQ ID NO: 2 or 4.

five additional amino acids (DNA sequence)

SEQ ID NO: 1

CGTTTCTCTGTTGTT 4-1BB costimulatory domain with five additional amino acids (DNA sequence)

SEQ ID NO: 2

CGTTTCTCTGTTGTTAAACGGGGCAGAAAGAAACTCCTGTATATATTCAA

ACAACCATTTATGAGACCAGTACAAACTACTCAAGAGGAAGATGGCTGTA

GCTGCCGATTTCCAGAAGAAGAAGAAGGAGGATGTGAACTG five additional amino acids (Amino acid sequence)

SEQ ID NO: 3

RFSVV 4-1BB costimulatory domain with five additional amino acids (Amino acid sequence)

SEQ ID NO: 4

RFSVVKRGRKKLLYIFKQPFMRPVQTTQEEDGCSCRFPEEEEGGCEL

In some embodiments, an extracellular binding domain of a CAR comprises an antigen-binding domain. In some embodiments, the antigen-binding domain specifically binds an antigen associated with a disease. In some embodiments, the antigen-binding domain specifically binds a tumor antigen. In some embodiments, the antigen-binding domain specifically binds to any number of targets, including surface antigens, cytoplasmic, or nuclear antigens. For example, the antigen binding domain can bind to BCMA, CD2, CD3, CD4, CD8, CD10, CD19, CD20, CD22, CD23, CD33, CD38, CD44, CD52, CD70, CD99, CD138, CD123, CD274, TIM-3, members of the epidermal growth factor receptor family (erb1, erb2, erb3, erb4 and mutants thereof), members of the ephrin receptor family (EphA1-10, EphB1-6), prostate specific antigens (e.g., prostate stem cell antigen PSCA, prostate specific membrane antigen PSMA), embryonic antigens (e.g. carcinoembryonic antigen CEA, fetal acethylcholine receptor), members of the vascular endothelia growth factor family (VEGFR 1-3), epithelia cell adhesion molecule EpCAM, alphafetoprotein AFP, members of the mucin protein family (e.g. MUC1, MUC16), follicle stimulating hormone receptor (FSHR), the human high molecular weight-melanoma-associated antigen (HMW-MAA), folate binding protein FBP, a-Folate receptor, ligands of the NKG2D receptor, members of the epithelia glycoprotein family (e.g. EGP-2, EGP-4), diasialogangliosides (e.g. GD2, GD3), members of the carbonic anhydrase family (e.g. CAIX), and members of the carbohydrate antigen family (e.g. Ley), including mutants of the named proteins and protein families. In some embodiments, the antigen-binding domain can bind to antibodies or fragments thereof that binds to cytoplasmic or nuclear antigens like the La/SSB antigen, members of the Rho family of GTPases, members of the high mobility group proteins and others. Likewise, the antigen binding domain can bind to the alpha and beta or the gamma and delta chains of a T cell receptor (TCR) or fragments thereof. In some embodiments, the antigen binding domain can bind to peptides presented by human leukocyte antigen class (HLA) I and II protein complexes. Examples are, but are not limited to, TCRs specific for peptides derived from proteins like the EGFR family, survivin, srylike high motility group box (SOX) protein family, melanoma-associated antigens (e.g. autoimmunogenic cancer/testis antigen NY-ESO-1, members of the melanoma antigen family A MAGEA, the preferentially expressed antigen in melanoma PRAME, gp100, MART-1), and leukemia-associated antigens (e.g., AML1-ETO, DEK-CAN, PML-RARalpha, Flt3-ITD, NPM1, AurA, Bcl-2, Bl-1, BMI1, BRAP, CML28, CML66, Cyclin A, Cyclin B1, Cyclin E, CYP1B1, ETO/MTG8, G250/CAIX, HOXA9, hTERT, Mc1-1, MAGE, Mesothelin, mHAg, Myeloperoxidase, MPP11, MUC1, NuSAP1, OFA/iLRP, PASD1, PRAME, Proteinase 3, RAGE-1, RGSS, RHAMM, SSX2IP, Syrvivin, Wilms tumor gene 1 (WT1)). The antigen binding domain can bind to cytokine receptors (e.g., IL-13 receptor, IL-22 receptor), NKG2D receptors (e.g., ULBP1, ULBP2), EGFR family members, or auto-reactive TCRs. In some embodiments, the antigen-binding domain specifically binds to tumor antigens. Examples are, but are not limited to, glypican-3 (GPC), malignancy variant receptor (MVR), HLA-DR (Human Leukocyte Antigen-D Related), AFP, CEA, CA-125, MUC-1, ETA, Tyrosinase, MAGE, Immature laminin receptor, TAG-72, HPV E6, HPV E7, BING-4, Calcium-activated chloride channel 2, Cyclin-B1, 9D7, Ep-CAM, EphA3, Her2/neu, Telomerase, Mesothelin, SAP-1, Survivin, NY-ESO-1/LAGE-1, PRAME, SSX-2, BRCA1/2, CDK4, CML66, or CD19. In some embodiments, an antigen-binding domain is or comprises an antibody agent. In some embodiments, an antigen-binding domain is or comprises an antibody agent that specifically binds to GPC3, MVR, HLA-DR, or CD19.

In some embodiments, the transmembrane domain is a transmembrane domain from a protein selected from 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3delta, CD3 epsilon, CD3 gamma, CD3 zeta, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell co-stimulator (ICOS), an integrin, ITGA4, ITGA6, ITGAD, ITGAE, ITGAL, ITGAM, ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1), an MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecule (a SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6. In some embodiments, the transmembrane domain is a transmembrane domain from CD8α. In some embodiments, the transmembrane domain comprises SEQ ID NO: 5. In some embodiments, the transmembrane domain includes a sequence that is at least 80%, 85%, 90%, 91%, 92%, 93%, 94%, 95%, 96%, 97%, 98%, 99%, or 100% identical to SEQ ID NO: 5.

CD8/Hinge/Transmembrane

SEQ ID NO: 5

ACCACGACGCCAGCGCCGCGACCACCAACACCGGCGCCCACCATCGCTAG

CCAGCCCCTGTCCCTGCGCCCAGAGGCGTGCCGGCCAGCGGCGGGGGGCG

CAGTGCACACGAGGGGGCTGGACTTCGCCTGTGATATCTACATCTGGGCG

CCCTTGGCCGGGACTTGTGGGGTCCTTCTCCTGTCACTGGTTATCACCCT

TTACTGC

In some embodiments, the intracellular domain further comprises an intracellular domain from CD3ζ. In some embodiments, the intracellular domain comprises SEQ ID NO: 6. In some embodiments, the intracellular domain includes a sequence that is at least 80%, 85%, 90%, 91%, 92%, 93%, 94%, 95%, 96%, 97%, 98%, 99%, or 100% identical to SEQ ID NO: 6.

CD3ζ

SEQ ID NO: 6

AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAA

In some embodiments, the CAR further comprises a T2A self-cleaving peptide. In some embodiments, the CAR further comprises a signal peptide or leader sequence. In some embodiments, the CAR further comprises a CD8α leader sequence. In some embodiments, the CAR further comprises a flag-tag sequence. In some embodiments, the CAR further comprises a hinge region. In some embodiments, the hinge region is a CD8α hinge. In some embodiments, the CAR further comprises SEQ ID NO: 7. In some embodiments, the CAR further comprises SEQ ID NO: 8. In some embodiments, the extracellular domain includes a sequence that is at least 80%, 85%, 90%, 91%, 92%, 93%, 94%, 95%, 96%, 97%, 98%, 99%, or 100% identical to SEQ ID NO: 7 or 8.

CD8α leader sequence

SEQ ID NO: 7

GGATCCATGGCCTTACCAGTGACCGCCTTGCTCCTGCCGCTGGCCTTGCT

GCTCCACGCCGCCAGGCCG

Flag-tag sequence

SEQ ID NO: 8

GACTACAAGGACGACGATGACAAG

GPC3 CAR

Glypican-3 (GPC3) is a cell surface protein encoded by the GPC3 gene in humans and an oncofetal antigen re-expressed in a high frequency of neoplastic hepatocytes (Vidali, et al., 2008, J hepatol 48:399-406). GPC3 is highly expressed in fetal liver and not expressed in normal adult liver tissue, but its expression is reactivated in hepatocellular carcinoma, and has close association with the development of liver cancer, where the detection rate of GPC3 expression is relatively high during early stage of liver cancer and increases along with the development of liver cancer. Further, GPC3 is also expressed in tumors such as melanoma, ovarian clear cell carcinoma, yolk sac tumor, neuroblastoma and other tumors. Considering its specifically high expression in hepatocellular carcinoma, melanoma and other tumors, GPC3 has emerged as a useful immunohistochemical diagnostic test (Anatelli, et al., 2008, Am J Clin Path 130:219-223) and potential biomarker (Aburatani, 2005, J Gastroenterol 40. S16:1-6).

GPC3 is a member of the proteoglycan family that functions as extracellular matrix in cell adhesion in organogenesis or as a receptor of a cell growth factor. The protein core of GPC3 comprises two subunits, and N-terminal subunit and a C-terminal subunit. A glycosyl phosphatidylinositol (GPI) anchor is added to serine at position 560 located on the carboxyl (C)-terminal side of GPC3. The GPI anchor plays a role in localizing GPC3 on cell surface through covalent binding to cell membrane lipid. Also, serine at position 495 and serine at position 509 of GPC3 are modified with a heparan sulfate chain (HS chain) wherein the HS chain is known to regulate a plurality of growth signal transduction pathways such as Wnt signal, FGF signal, and BMP signal transduction pathways. A growth signal transduction pathway involved is known to differ among the types of cancers. For example, in hepatocellular carcinoma (HCC), cells grow by the stimulation of the Wnt signal pathway.

The present disclosure provides, at least in part, GPC3 CAR polypeptides. In some embodiments, an extracellular binding domain of a GPC3 CAR comprises an antigen binding domain. In some embodiments, an antigen binding domain is or comprises an antibody agent. In some embodiments, an antigen binding domain is or comprises an antibody agent that specifically binds to GPC3.

In some embodiments, the chimeric antigen receptor (CAR) polypeptide includes: i) an extracellular antigen-binding domain comprising a light chain variable domain comprising a light chain CDR1 comprising SEQ ID NO: 9; a light chain CDR2 comprising SEQ ID NO: 10; and a light chain CDR3 comprising SEQ ID NO: 11; and a heavy chain variable domain comprising a heavy chain CDR1 comprising SEQ ID NO: 12; a heavy chain CDR2 comprising SEQ ID NO: 13; and a heavy chain CDR3 comprising SEQ ID NO: 14; ii) a transmembrane domain; and iii) an intracellular signaling domain, which leads to T cell activation when an antigen binds to the antibody agent.

| | SEQUENCE | SEQ ID NO: |
|---|---|---|
| Light chain CDR1 | RSSQSLVHSNGNTYLH | 9 |
| Light chain CDR2 | KVSNRFS | 10 |
| Light chain CDR3 | SQNTHVPPT | 11 |
| Heavy chain CDR1 | DYEMH | 12 |
| Heavy chain CDR2 | ALDPKTGDTAYSQKFKG | 13 |
| Heavy chain CDR3 | FYSYTY | 14 |

In some embodiments, the CAR polypeptide includes: i) an extracellular antigen-binding domain comprising a light chain variable domain comprising a sequence that is at least 80%, 85%, 90%, 91%, 92%, 93%, 94%, 95%, 96%, 97%, 98%, 99%, or 100% identical to SEQ ID NO: 15 and a heavy chain variable domain comprising a sequence that is at least 80%, 85%, 90%, 91%, 92%, 93%, 94%, 95%, 96%, 97%, 98%, 99%, or 100% identical to SEQ ID NO: 16; ii) a transmembrane domain; and iii) an intracellular signaling domain, which leads to T cell activation when an antigen binds to the antibody agent. In some embodiments, the CAR polypeptide includes: i) an extracellular antigen-binding domain comprising a light chain variable domain comprising a sequence that is at least 80%, 85%, 90%, 91%, 92%, 93%, 94%, 95%, 96%, 97%, 98%, 99%, or 100% identical to SEQ ID NO: 17 and a heavy chain variable domain comprising a sequence that is at least 80%, 85%, 90%, 91%, 92%, 93%, 94%, 95%, 96%, 97%, 98%, 99%, or 100% identical to SEQ ID NO: 18; ii) a transmembrane domain;

and iii) an intracellular signaling domain, which leads to T cell activation when an antigen binds to the antibody agent.

In some embodiments, the CAR polypeptide includes: i) an extracellular antigen-binding domain comprising a light chain variable domain comprising SEQ ID NO: 15 and a heavy chain variable domain comprising SEQ ID NO: 16; ii) a transmembrane domain; and iii) an intracellular signaling domain, which leads to T cell activation when an antigen binds to the antibody agent.

```
human GC33 light chain variable region
(Amino acid sequence)
                                       SEQ ID NO: 15
DVVMTQSPLSLPVTLGQPASISCRSSQSLVHSNGNTYLHWYQQRPGQSPR

LLIYKVSNRFSGVPDRFSGSGSGTDFTLKISRVEAEDVGVYYCSQNTHVP

PTFGSGTKLEIK

human GC33 heavy chain variable region
(Amino acid sequence)
                                       SEQ ID NO: 16
QVQLVQSGAEVKKPGASVKVSCKASGYTFTDYEMHWVRQAPGQGLEWIGA

LDPKTGDTAYSQKFKGRATLTADKSTSTAYMELSSLRSEDTAVYYCTRFY

SYTYWGQGTLVTVSS

human GC33 light chain variable region
(DNA sequence)
                                       SEQ ID NO: 17
GACGTCGTTATGACACAGAGTCCCCTCTCCTTGCCGGTGACCCTGGGTCA

GCCTGCGTCCATCTCTTGCAGATCCTCCCAGTCTCTGGTACACTCCAACG

GCAACACATACTTGCACTGGTACCAACAAAGACCTGGTCAGTCACCGCGA

CTTCTCATATATAAAGTTTCCAATAGGTTCAGTGGAGTGCCAGACAGGTT

CAGTGGTTCAGGATCAGGCACTGATTTCACGCTTAAAATCAGTCGGGTTG

AGGCGGAGGACGTAGGAGTTTACTATTGCAGCCAGAATACGCACGTGCCG

CCTACTTTTGGCTCTGGAACCAAGTTGGAAATAAAG

human GC33 heavy chain variable region
(DNA sequence)
                                       SEQ ID NO: 18
CAAGTGCAACTCGTACAATCAGGTGCTGAAGTCAAAAAGCCGGGAGCCTC

TGTTAAAGTGTCCTGTAAAGCCAGCGGCTACACCTTTACCGATTATGAGA

TGCACTGGGTTCGGCAGGCTCCGGGCCAAGGTCTGGAGTGGATCGGGGCT

CTTGACCCAAAGACGGGCGACACGGCTTATTCACAAAAATTCAAAGGTAG

GGCTACTCTGACTGCCGATAAGTCCACCAGCACCGCGTATATGGAGCTCT

CTAGCTTGCGAAGCGAGGACACGGCGGTGTACTATTGCACACGCTTCTAT

AGTTACACATATTGGGGTCAAGGCACGCTTGTGACCGTGTCTAGC
```

MVR CAR

Human Leukocyte Antigen-DR (HLA-DR) is a classic major histocompatibility complex II molecule (Shackelford, D. A. et al., 1982 Immunol. Rev. 66: 133-187). HLA-DR and its ligand, a peptide of 9 amino acids in length or longer, constitutes a ligand for the T cell receptor (TCR). HLA-DR molecules are upregulated in response to signaling. In the instance of an infection, the peptide (such as the staphylococcal enterotoxin I peptide) is bound into a DR molecule and presented to T-cell receptors found on T-helper cells. These cells then bind to antigens on the surface of B-cells stimulating B-cell proliferation.

The primary function of HLA-DR is to present peptide antigens, potentially foreign in origin, to the immune system for the purpose of eliciting or suppressing T-(helper)-cell responses that eventually lead to the production of antibodies against the same peptide antigen. HLA-DR is an αβ heterodimer, cell surface receptor, each subunit of which contains two extracellular domains, a membrane-spanning domain and a cytoplasmic tail. Both α and β chains are anchored in the membrane. The N-terminal domain of the mature protein forms an alpha-helix that constitutes the exposed part of the binding groove, the C-terminal cytoplasmic region interact with the other chain forming a beta-sheet under the binding groove spanning to the cell membrane. The majority of the peptide contact positions are in the first 80 residues of each chain.

HLA-DR has restricted expression on antigen presenting cells, e.g., dendritic cells, macrophages, monocytes, and B cells. Increased abundance of HLA-DR 'antigen' on the cell surface is often in response to stimulation, and, therefore, HLA-DR is also a marker for immune stimulation. Due to the high expression level of HLA-DR in B cell malignancies and the limited expression spectrum on normal cells, antibodies against HLA-DR have been developed and tested for B cell malignancies in preclinical and clinical studies. (Nagy, Z. A., et al. (2002) *Nat. Med.* 8: 801-807; DeNardo, G. L., et al. (2005) *Clin. Cancer Res.* 11: 7075s-7079s; Ivanov, A., et al. (2009) *J. Clin. Invest.* 119: 2143-2159; Lin, T. S., et al. (2009) *Leuk. Lymphoma* 50: 1958-1963). In a phase I/II trial, although the toxicity was not serious, further study was discontinued due to limited efficacy (Lin, T. S., et al. (2009) *Leuk. Lymphoma* 50: 1958-1963).

As used herein, the malignancy variant receptor (MVR) antibody agent recognizes a polymorphic region of HLA-DR (described in U.S. Patent Application Publication No. US 2016-0257762, which is herein incorporated by reference in its entirety). The present disclosure provides, at least in part, MVR CAR polypeptides. A schematic of exemplary MVR CAR constructs in accordance with the present disclosure is shown in FIG. 1. In some embodiments, an extracellular domain of a CAR comprises an antigen-binding domain. In some embodiments, an antigen-binding domain is or comprises an antibody agent. In some embodiments, an antigen-binding domain is or comprises an antibody agent that specifically binds to HLA-DR.

In some embodiments, the CAR polypeptide includes a single-chain variable fragment (scFv) form of an anti-MVR antibody agent. In some embodiments, the CAR polypeptide comprises SEQ ID NO: 19. In some embodiments, the CAR includes a sequence that is at least 80%, 85%, 90%, 91%, 92%, 93%, 94%, 95%, 96%, 97%, 98%, 99%, or 100% identical to SEQ ID NO: 19.

In some embodiments, the CAR polypeptide includes a single-chain variable fragment (scFv) form of an anti-MVR antibody agent. In some embodiments, the CAR polypeptide comprises SEQ ID NO: 20. In some embodiments, the CAR includes a sequence that is at least 80%, 85%, 90%, 91%, 92%, 93%, 94%, 95%, 96%, 97%, 98%, 99%, or 100% identical to SEQ ID NO: 20.

```
MVRL2H2 (Amino acid sequence)
                                       SEQ ID NO: 19
DIQMTQSPSSLSASVGDRVTITCKASDHINNWLAWYQQKPGKAPKLLISG

ATSLETGVPSRFSGSGSGKDYTLTISSLQPEDFATYYCQQYWSTPFTFGQ

GTKVEIKGGGGSGGGGSGGGGSQVQLQESGPGLVKPSETLSLTCTVSGFS

LSRYSVHWIRQPPGKGLEWLGMIWGGGSTDYNSALKSRLTISKDNSKNQV
```

-continued

```
SLKLSSVTAADTAVYYCARNEGDTTAGTWFAYWGQGTLVTVSS

MVRL2H2 (DNA sequence)
                                              SEQ ID NO: 20
GATATTCAGATGACCCAGTCCCCGAGCTCCCTGTCCGCCTCTGTGGGCGA

TAGGGTCACCATCACCTGCAAGGCCAGTGACCACATCAACAACTGGCTGG

CCTGGTATCAACAGAAACCAGGAAAAGCTCCGAAACTACTGATCAGCGGC

GCCACCTCTCTGGAAACCGGAGTCCCTTCTCGCTTCTCTGGTTCCGGATC

TGGGAAGGATTACACTCTGACCATCAGCAGTCTGCAGCCGGAAGACTTCG

CAACTTATTACTGTCAGCAGTACTGGTCCACCCCCTTCACCTTCGGACAG

GGTACCAAGGTGGAGATCAAAGGCGGAGGCGGATCTGGCGGCGGAGGAAG

TGGCGGAGGGGGATCTCAGGTGCAGCTGCAGGAGTCGGGCCCAGGACTGG

TGAAGCCTTCGGAGACCCTGTCCCTCACCTGCACTGTCTCTGGTTTCTCC

CTGAGTCGGTACTCTGTGCATTGGATCCGGCAGCCCCCAGGGAAGGGACT

GGAGTGGCTGGGGATGATCTGGGGAGGCGGCAGCACCGACTACAACAGCG

CCCTGAAGTCCCGACTGACCATATCAAAGGACAACTCCAAGAACCAGGTG

TCCTTGAAGCTGAGCTCTGTGACCGCTGCGGACACGGCCGTGTATTACTG

TGCGAGAAATGAGGGCGATACCACCGCCGGCACTTGGTTTGCCTATTGGG

GCCAGGGAACCCTGGTCACCGTCTCCTCA
```

CD19 CAR

CD19 is a biomarker for normal and neoplastic B cells, as well as follicular dendritic cells. CD19 is critically involved in establishing intrinsic B cell signaling thresholds through modulating both B cell receptor-dependent and independent signaling. Furthermore, CD19 functions as the dominant signaling component of a multimolecular complex on the surface of mature B cells, alongside complement receptor CD21, and the tetraspanin membrane protein CD81 (TAPA-1), as well as CD225, wherein CD19 also plays a critical role in maintaining the balance between humoral, antigen-induced response and tolerance induction.

The present disclosure provides, at least in part, CD19 CAR polypeptides. In some embodiments, an extracellular domain of a CAR comprises an antigen-binding domain. In some embodiments, an antigen-binding domain is or comprises an antibody agent. In some embodiments, an antigen-binding domain is or comprises an antibody agent that specifically binds to CD19.

In some embodiments, the CAR polypeptide includes a single-chain variable fragment (scFv) form of an anti-CD19 antibody agent. In some embodiments, the CAR polypeptide comprises SEQ ID NO: 21. In some embodiments, the CAR includes a sequence that is at least 80%, 85%, 90%, 91%, 92%, 93%, 94%, 95%, 96%, 97%, 98%, 99%, or 100% identical to SEQ ID NO: 21.

In some embodiments, the CAR polypeptide includes a single-chain variable fragment (scFv) form of an anti-CD19 antibody agent. In some embodiments, the CAR polypeptide comprises SEQ ID NO: 22. In some embodiments, the CAR includes a sequence that is at least 80%, 85%, 90%, 91%, 92%, 93%, 94%, 95%, 96%, 97%, 98%, 99%, or 100% identical to SEQ ID NO: 22.

```
CD19 (Amino acid sequence)
                                              SEQ ID NO: 21
DIQMTQTTSSLSASLGDRVTISCRASQDISKYLNWYQQKPDGTVKLLIYH
```

-continued

```
TSRLHSGVPSRFSGSGSGTDYSLTISNLEQEDIATYFCQQGNTLPYTFGG

GTKLEITGGGGSGGGGSGGGGSEVKLQESGPGLVAPSQSLSVTCTVSGVS

LPDYGVSWIRQPPRKGLEWLGVIWGSETTYYNSALKSRLTIIKDNSKSQV

FLKMNSLQTDDTAIYYCAKHYYYGGSYAMDYWGQGTSVTVSS

CD19 (DNA sequence)
                                              SEQ ID NO: 22
GACATCCAGATGACACAGACTACATCCTCCCTGTCTGCCTCTCTGGGAGA

CAGAGTCACCATCAGTTGCAGGGCAAGTCAGGACATTAGTAAATATTTAA

ATTGGTATCAGCAGAAACCAGATGGAACTGTTAAACTCCTGATCTACCAT

ACATCAAGATTACACTCAGGAGTCCCATCAAGGTTCAGTGGCAGTGGGTC

TGGAACAGATTATTCTCTCACCATTAGCAACCTGGAGCAAGAAGATATTG

CCACTTACTTTTGCCAACAGGGTAATACGCTTCCGTACACGTTCGGAGGG

GGGACCAAGCTGGAGATCACAGGTGGCGGTGGCTCGGGCGGTGGTGGGTC

GGGTGGCGGCGGATCTGAGGTGAAACTGCAGGAGTCAGGACCTGGCCTGG

TGGCGCCCTCACAGAGCCTGTCCGTCACATGCACTGTCTCAGGGGTCTCA

TTACCCGACTATGGTGTAAGCTGGATTCGCCAGCCTCCACGAAAGGGTCT

GGAGTGGCTGGGAGTAATATGGGGTAGTGAAACCACATACTATAATTCAG

CTCTCAAATCCAGACTGACCATCATCAAGGACAACTCCAAGAGCCAAGTT

TTCTTAAAAATGAACAGTCTGCAAACTGATGACACAGCCATTTACTACTG

TGCCAAACATTATTACTACGGTGGTAGCTATGCTATGGACTACTGGGGCC

AAGGAACCTCAGTCACCGTCTCCTCA
```

Nucleic Acids

As used herein, "nucleic acid" is used to include any compound and/or substance that comprises polynucleotides. Exemplary nucleic acids or polynucleotides can include, but are not limited to, ribonucleic acids (RNAs) and/or deoxyribonucleic acids (DNAs).

In some embodiments, nucleic acid constructs include regions that encode a CAR, wherein the CAR comprises: (a) an extracellular domain comprising an antigen-binding domain; (b) a transmembrane domain; and (c) an intracellular domain comprising an intracellular signaling domain from 4-1BB/CD137 and five additional amino acids. In some embodiments, nucleic acid constructs may be inserted into an expression vector or viral vector by methods known to the art, and nucleic acid molecules may be operably linked to an expression control sequence. Non-limiting examples of expression vectors include plasmid vectors, transposon vectors, cosmid vectors, and viral derived vectors (e.g., any adenoviral derived vectors (AV), cytomegaloviral derived (CMV) vectors, simian viral derived (SV40) vectors, adeno-associated virus (AAV) vectors, lentivirus vectors, and retroviral vectors). In some embodiments, the expression vector is a viral vector. In some embodiments, the viral vector is a lentiviral vector. In some embodiments, the expression vector further comprises a promoter operationally linked to the nucleic acid. In some embodiments, the promoter is a constitutive promoter. In some embodiments, the promoter is an inducible promoter. In some embodiments, the expression vector comprises SEQ ID NO: 23, 24, 25, 26, 27, and/or 28. In some embodiments, the expression vector includes a sequence that is at least 80%, 85%, 90%, 91%, 92%, 93%, 94%, 95%, 96%, 97%, 98%, 99%, or 100% identical to SEQ ID NO: 23, 24, 25, 26, 27, and/or 28.

EF1α-promoter

SEQ ID NO: 23

CGTGAGGCTCCGGTGCCCGTCAGTGGGCAGAGCGCACATCGCCCACAGTC
CCCGAGAAGTTGGGGGGAGGGGTCGGCAATTGAACCGGTGCCTAGAGAAG
GTGGCGCGGGGTAAACTGGGAAAGTGATGTCGTGTACTGGCTCCGCCTTT
TTCCCGAGGGTGGGGGAGAACCGTATATAAGTGCAGTAGTCGCCGTGAAC
GTTCTTTTTCGCAACGGGTTTGCCGCCAGAACACAGGTAAGTGCCGTGTG
TGGTTCCCGCGGGCCTGGCCTCTTTACGGGTTATGGCCCTTGCGTGCCTT
GAATTACTTCCACCTGGCTGCAGTACGTGATTCTTGATCCCGAGCTTCGG
GTTGGAAGTGGGTGGGAGAGTTCGAGGCCTTGCGCTTAAGGAGCCCCTTC
GCCTCGTGCTTGAGTTGAGGCCTGGCCTGGGCGCTGGGGCCGCCGCGTGC
GAATCTGGTGGCACCTTCGCGCCTGTCTCGCTGCTTTCGATAAGTCTCTA
GCCATTTAAAATTTTTGATGACCTGCTGCGACGCTTTTTTTCTGGCAAGA
TAGTCTTGTAAATGCGGGCCAAGATCTGCACACTGGTATTTCGGTTTTTG
GGGCCGCGGGCGGCGACGGGGCCCGTGCGTCCCAGCGCACATGTTCGGCG
AGGCGGGGCCTGCGAGCGCGGCCACCGAGAATCGGACGGGGGTAGTCTCA
AGCTGGCCGGCCTGCTCTGGTGCCTGGCCTCGCGCCGCCGTGTATCGCCC
CGCCCTGGGCGGCAAGGCTGGCCCGGTCGGCACCAGTTGCGTGAGCGGAA
AGATGGCCGCTTCCCGGCCCTGCTGCAGGGAGCTCAAAATGGAGGACGCG
GCGCTCGGGAGAGCGGGCGGGTGAGTCACCCACACAAAGGAAAAGGGCCT
TTCCGTCCTCAGCCGTCGCTTCATGTGACTCCACTGAGTACCGGGCGCCG
TCCAGGCACCTCGATTAGTTCTCGAGCTTTTGGAGTACGTCGTCTTTAGG
TTGGGGGGAGGGGTTTTATGCGATGGAGTTTCCCCACACTGAGTGGGTGG
AGACTGAAGTTAGGCCAGCTTGGCACTTGATGTAATTCTCCTTGGAATTT
GCCCTTTTTGAGTTTGGATCTTGGTTCATTCTCAAGCCTCAGACAGTGGT
TCAAAGTTTTTTTCTTCCATTTCAGGTGTCGTGA

U5 repeat

SEQ ID NO: 24

AGTAGTGTGTGCCCGTCTGTTGTGTGACTCTGGTAACTAGAGATCCCTCA
GACCCTTTTAGTCAGTGTGGAAAATCTCTAGCAG

Gag/Pol

SEQ ID NO: 25

CGAACAGGGACTTGAAAGCGAAAGGGAAACCAGAGGAGCTCTCTCGACGC
AGGACTCGGCTTGCTGAAGCGCGCACGGCAAGAGGCGAGGGGCGGCGACT
GGTGAGTACGCCAAAAATTTTGACTAGCGGAGGCTAGAAGGAGAGAGATG
GGTGCGAGAGCGTCAGTATTAAGCGGGGGAGAATTAGATCGCGATGGGAA
AAAATTCGGTTAAGGCCAGGGGGAAAGAAAAAATATAAATTAAAACATAT
AGTATGGGCAAGCAGGGAGCTAGAACGATTCGCAGTTAATCCTGGCCTGT
TAGAAACATCAGAAGGCTGTAGACAAATACTGGGACAGCTACAACCATCC
CTTCAGACAGGATCAGAAGAACTTAGATCATTATATAATACAGTAGCAAC
CCTCTATTGTGTGCATCAAAGGATAGAGATAAAAGACACCAAGGAAGCTT
TAGACAAGATAGAGGAAGAGCAAAACAAAAGTAAGACCACCGCACAGCAA
GCGGCCGCTGATCTTCAGACCTGGAGGAGGAGATATGAGGGACAATTGGA
GAAGTGAATTATATAAATATAAAGTAGTAAAAATTGAACCATTAGGAGTA

-continued

GCACCCACCAAGGCAAAGAGAAGAGTGGTGCAGAGAGAAAAAAGAGCAGT
GGGAATAGGAGCTTTGTTCCTTGGGTTCTTGGGAGCAGCAGGAAGCACTA
TGGGCGCAGCGTCAATGACGCTGACGGTACAGGCCAGACAATTATTGTCT
GGTATAGTGCAGCAGCAGAACAATTTGCTGAGGGCTATTGAGGCGCAACA
GCATCTGTTGCAACTCACAGTCTGGGGCATCAAGCAGCTCCAGGCAAGAA
TCCTGGCTGTGGAAAGATACCTAAAGGATCAACAGCTCCTGGGGATTTGG
GGTTGCTCTGGAAAACTCATTTGCACCACTGCTGTGCCTTGGAATGCTAG
TTGGAGTAATAAATCTCTGGAACAGATTTGGAATCACACGACCTGGATGG
AGTGGGACAGAGAAATTAACAATTACACAAGCTTAATACACTCCTTAATT
GAAGAATCGCAAAACCAGCAAGAAAAGAATGAACAAGAATTATTGGAATT
AGATAAATGGGCAAGTTTGTGGAATTGGTTTAACATAACAAATTGGCTGT
GGTATATAAAATTATTCATAATGATAGTAGGAGGCTTGGTAGGTTTAAGA
ATAGTTTTTGCTGTACTTTCTATAGTGAATAGAGTTAGGCAGGGATATTC
ACCATTATCGTTTCAGACCCACCTCCCAACCCCGAGGGGACCCGACAGGC
CCGAAGGAATAGAAGAAGAAGGTGGAGAGAGAGACAGAGACAGATCCATT
CGATTAGTGAACGGATCTCGACGGTAT cPPT

SEQ ID NO: 26

TAGACTGTAGCCCAGGAATATGGCAGCTAGATTGTACACATTTAGAAGGA
AAAGTTATCTTGGTAGCAGTTCATGTAGCCAGTGGATATATAGAAGCAGA
AGTAATTCCAGCAGAGACAGGGCAAGAAACAGCATACTTCCTCTTAAAAT
TAGCAGGAAGATGGCCAGTAAAAACAGTACATACAGACAATGGCAGCAAT
TTCACCAGTACTACAGTTAAGGCCGCCTGTTGGTGGGCGGGGATCAAGCA
GGAATTTGGCATTCCCTACAATCCCCAAAGTCAAGGAGTAATAGAATCTA
TGAATAAAGAATTAAAGAAAATTATAGGACAGGTAAGAGATCAGGCTGAA
CATCTTAAGACAGCAGTACAAATGGCAGTATTCATCCACAATTTTAAAAG
AAAAGGGGGGATTGGGGGGTACAGTGCAGGGGAAAGAATAGTAGACATAA
TAGCAACAGACATACAAACTAAAGAATTACAAAAACAAATTACAAAAATT
CAAAATTTTCGGGTTTATTACAGGGACAGCAGAGATCCAGTTTGGCT

Woodchuck/PRE

SEQ ID NO: 27

ATCAACCTCTGGATTACAAAATTTGTGAAAGATTGACTGGTATTCTTAAC
TATGTTGCTCCTTTTACGCTATGTGGATACGCTGCTTTAATGCCTTTGTA
TCATGCTATTGCTTCCCGTATGGCTTTCATTTTCTCCTCCTTGTATAAAT
CCTGGTTGCTGTCTCTTTATGAGGAGTTGTGGCCCGTTGTCAGGCAACGT
GGCGTGGTGTGCACTGTGTTTGCTGACGCAACCCCCACTGGTTGGGGCAT
TGCCACCACCTGTCAGCTCCTTTCCGGGACTTTCGCTTTCCCCCTCCCTA
TTGCCACGGCGGAACTCATCGCCGCCTGCCTTGCCCGCTGCTGGACAGGG
GCTCGGCTGTTGGGCACTGACAATTCCGTGGTGTTGTCGGGGAAGCTGAC
GTCCTTTCCATGGCTGCTCGCCTGTGTTGCCACCTGGATTCTGCGCGGGA
CGTCCTTCTGCTACGTCCCTTCGGCCCTCAATCCAGCGGACCTTCCTTCC
CGCGGCCTGCTGCCGGCTCTGCGGCCTCTTCCGCGTCTTCGCCTTCGCCC

-continued

```
TCAGACGAGTCGGATCTCCCTTTGGGCCGCCTCCCCGCCTG

R/region
                                                  SEQ ID NO: 28
GGGTCTCTCTGGTTAGACCAGATCTGAGCCTGGGAGCTCTCTGGCTAACT

AGGGAACCCACTGCTTAAGCCTCAATAAAGCTTGCCTTGAGTGCTTCA
```

A lentiviral vector is derived from a lentivirus. Lentiviral vectors are based on the single-stranded RNA lentiviruses, which are a subclass of retrovirus. They combine the advantages of midrange cloning capacity with stable gene expression, wherein they are able to transduce dividing and non-dividing cells, including neurons. Upon infection, the lentiviral genome integrates transgenes into the host genome and promotes long-term gene expression. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art.

In some embodiments, nucleic acid molecules are inserted into a vector that is able to express a CAR of the present disclosure when introduced into an engineered immune cell. In some embodiments, an engineered immune cell is a T cell.

Production of CAR-T Cells

Provided herein are methods for producing immune cells comprising a CAR. In some embodiments, the immune cell where a CAR is introduced therein is a human immune cell. In some embodiments, the immune cell is an autologous human immune cell. In some embodiments, the immune cell is an allogeneic human immune cell. In some embodiments, the immune cell is a $CD4^+$ T cell (helper T cell, TH cell), a $CD8^+$ T cell (cytotoxic T cell, CTL), a memory T cell, a regulatory T cell (Treg cell), an apoptotic T cell, but is not limited thereto. In some embodiments, the immune cell is an NK cell.

In some embodiments, viral infection of an immune cell can comprise transfecting a host cell (e.g., 293T cell, PBMC, Plat-GP cell, or PA317) with the CAR expression vector and a packaging plasmid to prepare recombinant viruses and infecting the immune cell with the recombinant viruses. The viral infection method may be performed by any method known in the art. In some embodiments, transfer of the CAR expression vector to the immune cell can be confirmed by examining the expression of the CAR by flow cytometry, Northern blotting, Southern blotting, PCR (e.g, RT-PCR), ELISA, or Western blotting, or examining the expression of a marker gene inserted in the vector.

In some embodiments, the present disclosure provides methods of producing an engineered immune cell, comprising: introducing into an immune cell (i) a nucleic acid encoding a CAR, wherein the CAR comprises (a) an extracellular domain comprising an antigen-binding domain; (b) a transmembrane domain; and (c) an intracellular domain comprising a costimulatory endodomain, wherein the costimulatory endodomain comprises an intracellular signaling domain from 4-1BB/CD137 and five additional amino acids, or (ii) a vector comprising the nucleic acid encoding a CAR, wherein the CAR comprises (a) an extracellular domain comprising an antigen-binding domain; (b) a transmembrane domain; and (c) an intracellular domain comprising a costimulatory endodomain, wherein the costimulatory endodomain comprises an intracellular signaling domain from 4-1BB/CD137 and five additional amino acids.

In some embodiments, to increase immunological efficacy in the cytoplasmic signal domain 4-1BB, 5 amino acids are added in the 4-1BB cytoplasmic domain used in producing a CAR as a costimulatory signal factor. In some embodiments, the completed construct comprises an antigen-binding domain, which is an scFv; an EF1-α promoter; a hinge region and a transmembrane domain of human CD8; and an intracellular signaling domain. In particular, the intracellular signaling domain comprises a stimulatory domain and a costimulatory signaling domain. In some embodiments, the transmembrane domain can include the alpha, beta or zeta chain of the T cell receptor, or one or more of CD28, CD45, CD4, CD5, CD8, CD9, CD 16, CD22, CD33, CD37, CD64, CD80, CD86, CD134, CD137 or CD154, but it is not limited thereto. In some embodiments, the transmembrane domain includes CD8. In some embodiments, intracellular signaling domains include the costimulatory signaling domains in the CD3zeta primary signaling domain, selected from among CD28, OX40, CD27, ICAM-1, ICOS (CD278), and 4-1BB/CD137. In some embodiments, the costimulatory domain comprises 4-1BB to which 5 consecutive amino acids were added. In some embodiments, the costimulatory domain is linked to CD3zeta.

In some embodiments, a method of producing an engineered immune cell of the present disclosure further comprises culturing the engineered immune cell in vitro for at least 3 days, 4 days, 5 days, 6 days, 7 days, 8 days, 9 days, 10 days, 11 days, or 12 days.

In some embodiments, the method of producing an engineered immune cell further comprises, after the introducing step, culturing the engineered immune cell. In some embodiments, the method of producing an engineered immune cell further comprises, before the introducing step, obtaining the immune cell from a subject.

Any method known in the art for expressing a CAR in immune cells can be used in the context of the present disclosure. For example, there are various nucleic acid vectors for expression known in the art, such as linear polynucleotides, polynucleotides to which an ionic or amphiphilic compound is bound, plasmids, or viral vectors, though the present disclosure is not limited thereto. In some embodiments, a vector for expression of a CAR in immune cells may be or include an autonomously replicating plasmid or virus or derivative thereof. Viral vectors can include, but are not limited to adenovirus vector, adeno-associated viral vector, retrovirus vector, etc. In some embodiments a lentivirus vector, which is a retroviral vector, can be used. In some embodiments, a vector is a non-plasmid and a non-viral compound, such as, for example, a liposome.

The present disclosure encompasses the recognition that CAR-T cells, generated by the methods described herein may be therapeutically useful (e.g., for the treatment of cancer).

Therapeutic Applications

Provided herein are methods of treating a subject having a cancer or other malignancy, wherein the method comprises administering to a subject a composition that comprises or delivers an immune cell comprising a CAR. In some embodiments, the cancer is an anti-glypican-3-associated cancer. In some embodiments, the cancer is an anti-CD19-associated cancer. In some embodiments, the cancer is an anti-MVR-associated cancer.

Cancer can refer to a broad group of diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. Cancer or cancer tissue may include a tumor.

An "anti-glypican-3-associated cancer" is a cancer that is characterized by a cancer cell having glypican-3 present on its surface. GPC3, a membrane-bound heparan sulfate proteoglycan, is overexpressed in approximately 70% to 80% of hepatocellular carcinomas, but is not expressed commonly in healthy tissues. In addition, GPC3 overexpression is found in several tumors, such as but not limited to hepatocellular carcinomas, hepatoblastoma, germ cell tumors (e.g., yolk sac tumors, choriocarcionomas), Wilms tumor, gastric carcinoma, non-small lung cancer, and thyroid cancer.

An "anti-CD19-associated cancer" is a cancer that is characterized by CD19 expression, wherein CD19 shows an essential role in B cell development and maturation. CD19 expression is highly conserved on most B cell tumors. It is expressed in most acute lymphoblastic leukemia (ALL), chronic lymphocytic leukemia (CLL) and B cell lymphomas.

An "anti-MVR-associated cancer" is characterized by cancer cells with increased expression of HLA-DR antigen relative to a non-cancer cell from a subject. In some embodiments, a cancer with higher expression of HLA-DR antigen can include, but are not limited to, bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, and prostate cancer. In some embodiments, diseases associated with HLA-DR expression include, but are not limited to, atypical and/or non-classical cancers, malignancies, precancerous conditions or proliferative diseases expressing HLA-DR, or any combination thereof.

In some embodiments, a cancer for treatment by a method of the present disclosure can include, but is not limited to, carcinoma, lymphoma (e.g., Hodgkin's and non-Hodgkin's lymphomas), blastoma, sarcoma, and leukemia. In some embodiments, cancer may include squamous cell carcinoma, small cell lung cancer, non-small cell lung cancer, lung adenocarcinoma, squamous cell carcinoma of the lung, peritoneal cancer, hepatocellular carcinoma, gastric cancer, pancreatic cancer, glioma, cervical cancer, ovarian cancer, liver cancer, bladder cancer, hepatocellular carcinoma, breast cancer, colon cancer, colorectal cancer, endometrial or uterine carcinoma, salivary carcinoma, kidney cancer, prostate cancer, vulvar cancer, thyroid cancer, liver carcinoma, leukemia and other lymphoproliferative disorders, and various types of head and neck cancer.

In some embodiments, a cancer suitable for treatment by methods of the present disclosure is a hematologic cancer. In some embodiments, a hematologic cancer is a leukemia. In some embodiments, a cancer is selected from the group consisting of one or more acute leukemias including but not limited to B-cell acute lymphoid leukemia ("BALL"), T-cell acute lymphoid leukemia ("TALL"), acute lymphoid leukemia (ALL); one or more chronic leukemias including but not limited to chronic myelogenous leukemia (CIVIL), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells.

In some embodiments, a cancer for treatment by methods of the present disclosure is a B cell lymphoma (i.e., a malignant lymphoma of B cell origin). B cell lymphomas include Hodgkin's lymphoma and non-Hodgkin's lymphoma, diffuse large B cell lymphoma (DLBCL), follicular lymphoma, mucosa-associated lymphatic tissue lymphoma (MALT), chronic lymphocytic leukemia, mantle cell lymphoma (MCL), burkitt lymphoma, mediastinal large B cell lymphoma, waldenstrom macroglobulinemia, nodal marginal zone B cell lymphoma (NMZL), splenic marginal zone lymphoma (SMZL), intravascular large B-cell lymphoma, primary effusion lymphoma, lymphomatoid granulomatosis, and AIDS-related lymphoma, but is not particularly limited thereto as long as it is lymphoma of B cell origin.

The immune cells (e.g., CAR-T cells) may be administered at a therapeutically effective amount to a patient in need thereof. For example, a therapeutically effective amount of the immune cells (e.g. CAR-T cells) may be at least about $10^4$ cells, at least about $10^5$ cells, at least about $10^6$ cells, at least about $10^7$ cells, at least about $10^8$ cells, at least about $10^9$, or at least about $10^{10}$. In some embodiments, a therapeutically effective amount of T cells is about $10^4$ cells, about $10^5$ cells, about $10^6$ cells, about $10^7$ cells, or about $10^8$ cells. In some embodiments, the therapeutically effective amount of the T cells is between about $0.4\times10^8$ and about $2\times10^8$ T cells. In some embodiments, the therapeutically effective amount of the T cells is about $0.4\times10^8$, about $0.5\times10^8$, about $0.6\times10^8$, about $0.7\times10^8$, about $0.8\times10^8$, about $0.9\times10^8$, about $1.0\times10^8$, about $1.1\times10^8$, about $1.2\times10^8$, about $1.3\times10^8$, about $1.4\times10^8$, about $1.5\times10^8$, about $1.6\times10^8$, about $1.7\times10^8$, about $1.8\times10^8$, about $1.9\times10^8$, or about $2.0\times10^8$ T cells.

In some embodiments, a therapeutically effective amount of the CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In some embodiments, a therapeutically effective amount of immune cells (e.g., CAR-T cells) is between about $1\times10^6$ and about $2\times10^6$ T cells per kg body weight up to a maximum dose of about $1\times10^8$ T cells. In some embodiments, the therapeutically effective amount of the T cells is about $1\times10^6$ or about $2\times10^6$ T cells per kg body weight up to a maximum dose of about $1\times10^8$ T cells.

The number of cells will depend upon the ultimate use for which the composition is intended as will the type of cells included therein. For example, in some embodiments, a population of T cells comprising a CAR will contain greater than 10%, greater than 15%, greater than 20%, greater than 25%, greater than 30%, or greater than 35% of such cells. In some embodiments, a population of T cells comprising a CAR will contain 10% to 50%, 15% to 45%, 20% to 40%, 25% to 35%, or 20% to 30% of such T cells. In some embodiments, a population of T cells for administration is in a volume of a liter or less. In some embodiments, T cells for administration are in a volume of less than 500 ml, less than 250 ml, or 100 ml or less. In some embodiments, a density of the desired T cells is typically greater than $10^6$ cells/ml and generally is greater than $10^7$ cells/ml, generally $10^8$ cells/ml or greater. A clinically relevant number of immune cells can be apportioned into multiple infusions that cumulatively equal or exceed $10^7$ cells, $10^8$ cells, $10^9$ cells, $10^{10}$ cells, $10^{11}$ cells, or $10^{12}$ cells.

In some embodiments, a composition may be administered to a patient parenterally. In some embodiments, a composition that comprises or delivers a T cell comprising a CAR may be parenterally administered to a patient in one or multiple administrations. In some embodiments, a composition that comprises or delivers a T cell comprising a CAR may be parenterally administered to a patient once every day, once every 2 to 7 days, once every week, once every two weeks, once every month, once every three months, or once every 6 months.

In some embodiments, the present disclosure provides methods of treating a cancer in a subject in need thereof, the method comprising administering to the subject an engineered immune cell comprising a CAR, wherein the CAR comprises (a) an extracellular domain comprising an antigen-binding domain; (b) a transmembrane domain; and (c) an intracellular domain comprising a costimulatory endodomain, wherein the costimulatory endodomain comprises an intracellular signaling domain from 4-1BB/CD137 and five additional amino acids.

In some embodiments, the subject has previously been administered one or more additional anticancer therapies selected from the group consisting of: ionizing radiation, a chemotherapeutic agent, a therapeutic antibody, and a checkpoint inhibitor. In some embodiments, the subject has been identified or diagnosed as having a cancer.

Pharmaceutical Compositions

In some embodiments, the present disclosure provides pharmaceutical compositions that include a T cell comprising a CAR, wherein the CAR comprises (a) an extracellular domain comprising an antigen-binding domain; (b) a transmembrane domain; and (c) an intracellular domain comprising a costimulatory endodomain, wherein the costimulatory endodomain comprises an intracellular signaling domain from 4-1BB/CD137 and five additional amino acids, and a pharmaceutically acceptable carrier. In some embodiments, a T cell comprising the CAR is an autologous T cell. In some embodiments, a pharmaceutical composition can include a buffer, a diluent, solubilizer, emulsifier, preservative, adjuvant, an excipient, or any combination thereof. In some embodiments, a composition, if desired, can also contain one or more additional therapeutically active substances.

In some embodiments, T cells of the present disclosure are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

In some embodiments, compositions are formulated for parenteral administration. For example, a pharmaceutical composition provided herein may be provided in a sterile injectable form (e.g., a form that is suitable for subcutaneous injection or intravenous infusion). For example, in some embodiments, a pharmaceutical composition is provided in a liquid dosage form that is suitable for injection. In some embodiments, a pharmaceutical composition is provided as powders (e.g., lyophilized and/or sterilized), optionally under vacuum, which can be reconstituted with an aqueous diluent (e.g., water, buffer, salt solution, etc.) prior to injection. In some embodiments, a pharmaceutical composition is diluted and/or reconstituted in water, sodium chloride solution, sodium acetate solution, benzyl alcohol solution, phosphate buffered saline, etc. In some embodiments, a powder should be mixed gently with the aqueous diluent (e.g., not shaken).

In some embodiments, a T cell comprising the CAR and/or a nucleic acid encoding the CAR of the present disclosure is formulated with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. A vehicle or lyophilized powder can contain additives that maintain isotonicity (e.g., sodium chloride, mannitol) and chemical stability (e.g., buffers and preservatives). In some embodiments, a formulation is sterilized by known or suitable techniques. A pharmaceutical composition may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, MD, 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, a composition including a population of T cells comprising the CAR and/or a nucleic acid encoding the CAR of the present disclosure is stably formulated. In some embodiments, a stable formulation of a population of T cells comprising the CAR and/or a nucleic acid encoding the CAR of the present disclosure may comprise a phosphate buffer with saline or a chosen salt, as well as preserved solutions and formulations containing a preservative as well as multi-use preserved formulations suitable for pharmaceutical or veterinary use. Preserved formulations contain at least one known preservative or optionally selected from the group consisting of at least one phenol, m-cresol, peresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

In some embodiments, a pharmaceutical composition is provided in a form that can be refrigerated and/or frozen. In some embodiments, a pharmaceutical composition is provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of compositions including an antibody agent for longer than the specified time results in degradation of the antibody agent. Liquid dosage forms and/or reconstituted solutions may comprise particulate matter and/or discoloration prior to administration. In some embodiments, a solution should not be used if discolored or cloudy and/or if particulate matter remains after filtration. General considerations in the formulation and/or manufacture of pharmaceutical agents may be found, for example, in Remington: The Science and Practice of Pharmacy $21^{st}$ ed., Lippincott Williams & Wilkins, 2005.

In some embodiments, a pharmaceutical composition including a T cell comprising the CAR and/or a nucleic acid encoding the CAR of the present disclosure can be included in a container for storage or administration, for example, an vial, a syringe (e.g., an IV syringe), or a bag (e.g., an IV bag). A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Kits

The present disclosure further provides a kit comprising one or more containers filled with at least one CAR and/or a nucleic acid encoding a CAR as described herein. Kits may be used in any applicable method, including, for example, therapeutic methods, diagnostic methods, cell proliferation and/or isolation methods, etc. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In some embodiments, a kit may include one or more reagents for detection (e.g., detection of a CAR and/or a nucleic acid encoding a CAR. In some embodiments, a kit may include a CAR and/or a nucleic acid encoding a CAR in a detectable form (e.g., covalently associated with detectable moiety or entity). In some embodiments, one or more CARs and/or nucleic acids encoding a CAR as provided herein may be included in a kit used for treatment of subjects. In some embodiments, a CAR and/or a nucleic acid encoding a CAR as provided herein may be included in a kit used for preparing an autologous T cell expressing the CAR.

In some embodiments, a kit may provide one, two, three, four or more antigen specific antibody agents, where each is suitable for cloning into a CAR construct. In some embodiments, a kit may provide other reagents for assaying binding affinity of an antibody agent and/or CAR and/or a CAR T cell for a T cell identified or isolated from a subject. In some embodiments, a kit may provide other reagents for assaying functional avidity of an antibody agent and/or CAR and/or a CAR T cell for a T cell of a subject.

EXAMPLES

The disclosure is further described in the following examples, which do not limit the scope of the disclosure described in the claims.

Example 1—GPC3 Lentiviral Transfer Plasmid

Figure 2:
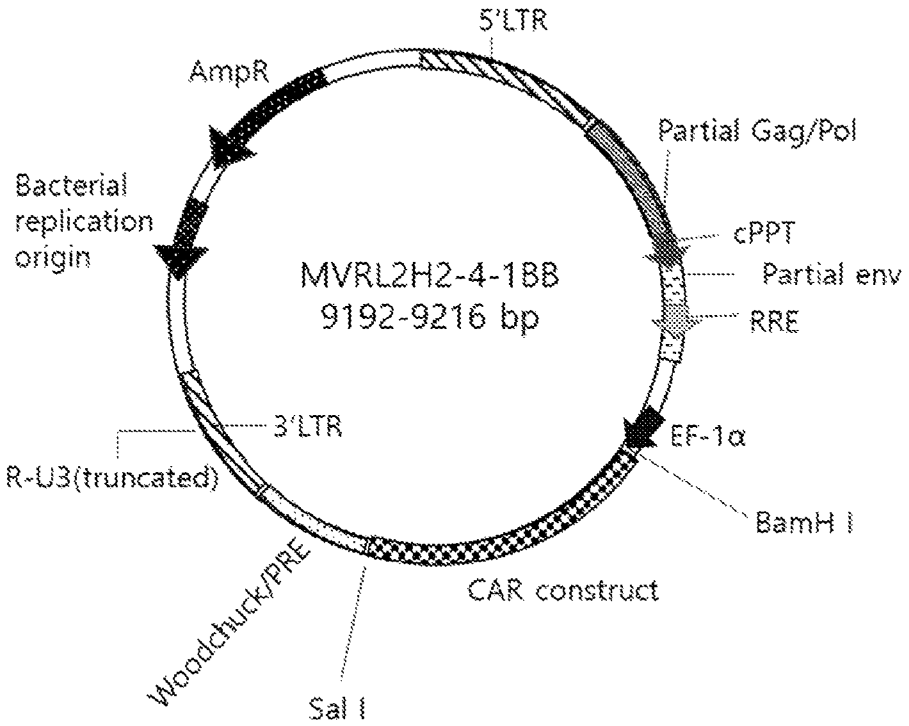
FIG. 2 shows exemplary enzyme mapping results after MVRL2H2-4-1BB cloning.

A DNA construct encoding a single-chain variable fragment (scFv) form (FIG. 2) of a humanized anti-GC33 antibody agent was generated by connecting the VH and VL regions, using standard DNA cloning techniques known to the art. The lentiviral transfer plasmid used herein is shown in Table 1.

TABLE 1

| Lentiviral Transfer Vector | | | |
|---|---|---|---|
| scFv | Intracellular Domain | Selectable marker | Transfer vector |
| huGC33 VH-VL | euBBz | Flag | pELPS4 |
| huGC33 VH-VL | BBz | Flag | pELPS3 |

Figure 3:
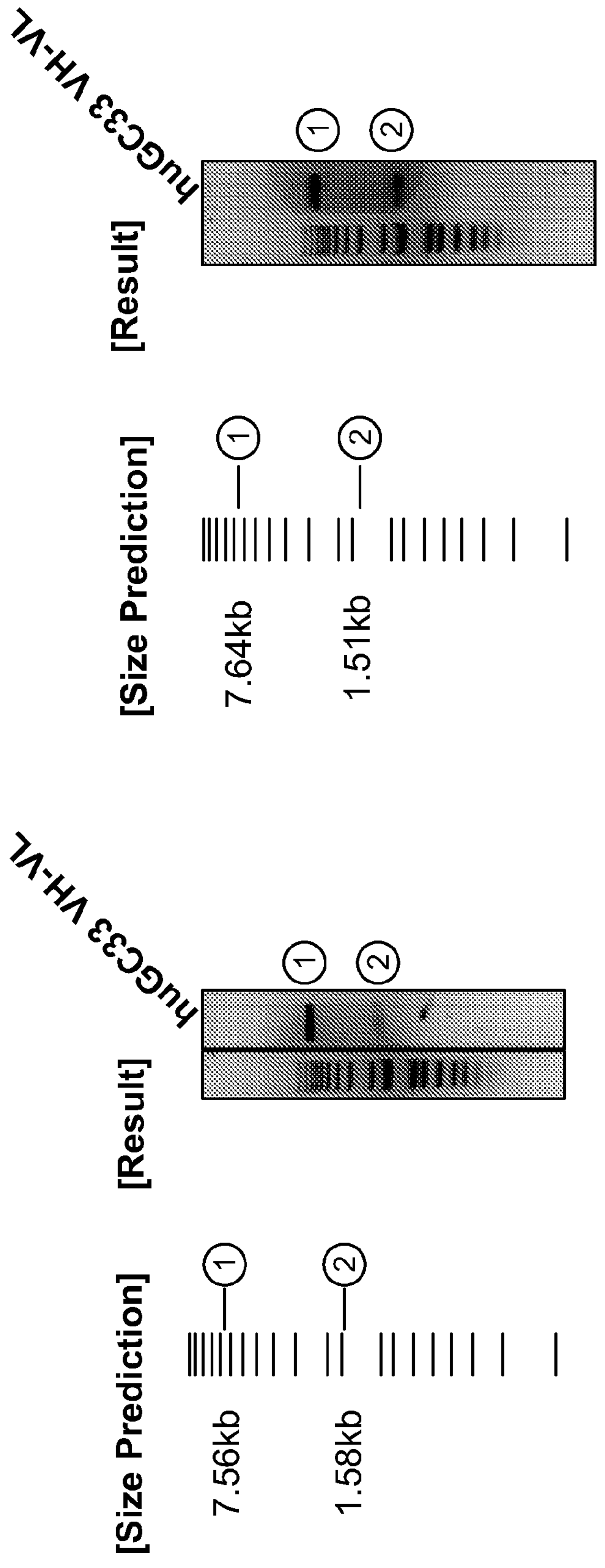
FIG. 3 shows restriction enzyme digestion results of huGC33(VH-VL)-euBBz, wherein the expected size is marked on the DNA ladders and the results are shown in gel electrophoresis images.

The huGC33 VH-VL-scFv was cloned into a lentiviral vector, pELPS4-MVRL2H2-euBBz, wherein pELPS4-MVRL2H2-euBBz is a lentiviral vector including a costimulatory domain 4-1BB with five additional amino acids. The lentivirus vector construct, pELPS4-huGC33 VH-VL was digested with restriction enzymes, wherein restriction enzyme digestion results are shown in FIG. 3.

Figure 4:
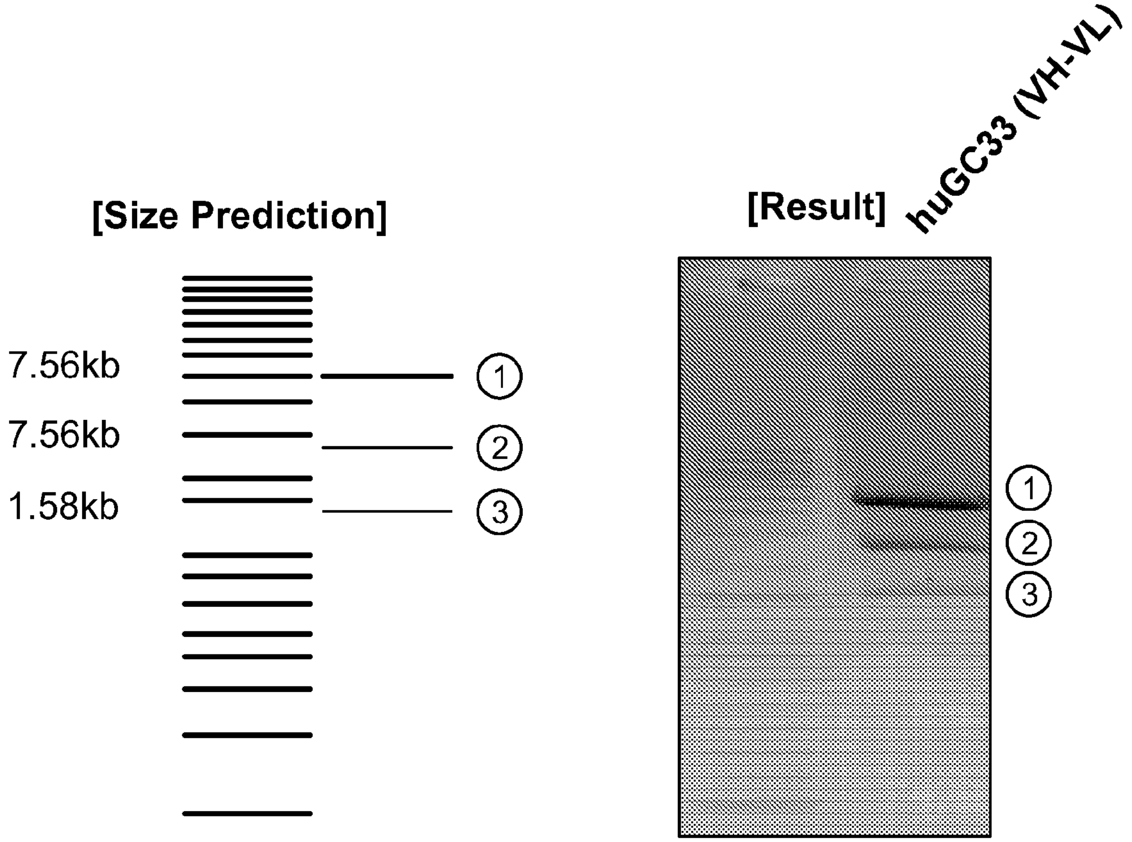
FIG. 4 shows restriction enzyme digestion results of huGC33(VH-VL)-BBz, wherein the expected size is marked on the DNA ladder and the result is shown in gel electrophoresis image.

To create a CAR construct without the five additional amino acids to the 4-1BB costimulatory domain, the huGC33 VH-VL-scFv was cloned into a lentiviral vector, pELPS2-CD19-BBz, wherein pELPS2-CD19-BBz is a lentiviral vector including a costimulatory domain 4-1BB without five additional amino acids. The lentivirus vector construct, huGC33(VH-VL)-BBz was digested with restriction enzymes, wherein restriction enzyme digestion results are shown in FIG. 4.

Example 2—Pharmaceutical Composition of GPC3 CAR-T Cells

PBMCs were thawed and activated by placing the PBMC cryovials ($5\times10^7$ cells/1 mL/vial) in a water bath for 2-3 minutes. 10 mL CAR-T cell culture media and 1 mL PBMC was placed in a 50 mL conical tube and centrifuged at 1500 rpm for 5 minutes. The supernatant was removed and the CAR-T cells were counted after resuspending the cells in 5 mL in fresh media. Fresh cell media was added to adjust the cell density to be $1\times10^6$ cells/mL. 10 μL of T cell activation bead was added for every $1\times10^6$ cells and IL-2 was supplemented to the media. The cell culture medium was cultured in a T75 flask at $CO_2$ 5% and 37° C. in an incubator.

CAR-T cells were then generated by spinoculation of activated T cells with CAR-encoding lentivirus. Activated PBMCs were counted from the cell culture and the cells were seeded in a 24 well plate in the presence of 500 μL cell media with lentivirus. After spinoculation transduction, the transduced cells from 1 well were cultured in cell culture media supplemented with IL-2.

Figure 5A:
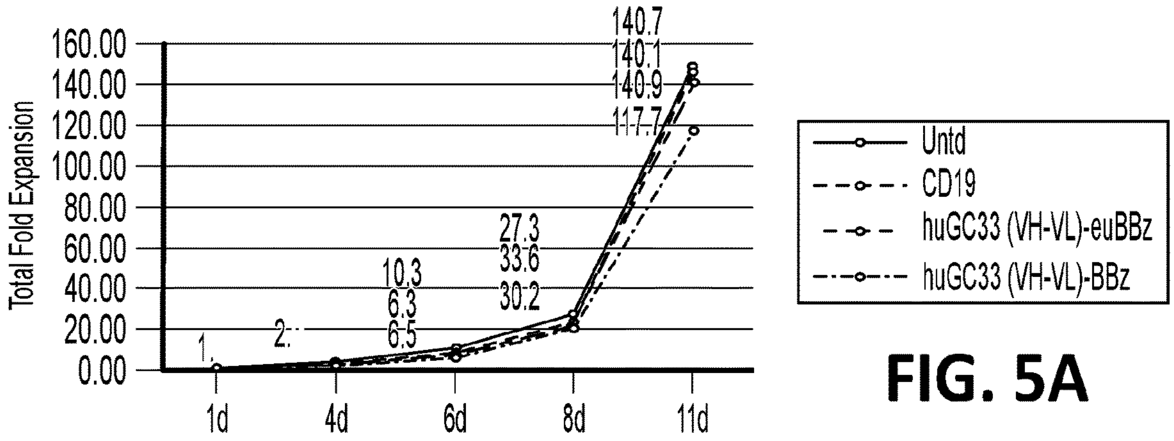
FIG. 5A is a graph showing total fold expansion of the CAR-T cells over a 11 day period in vitro.
Figure 5B:
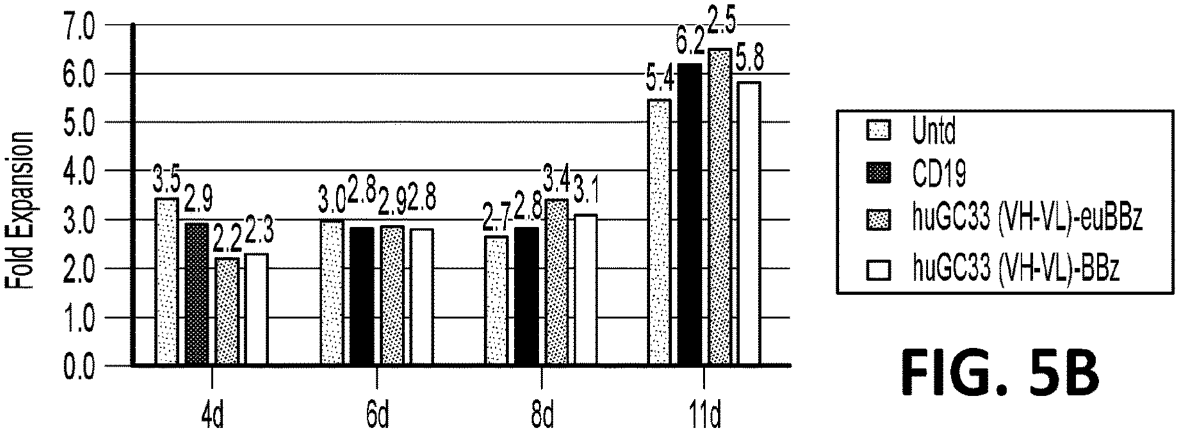
FIG. 5B is a graph comparing fold expansion of the CAR-T cells in vitro.
Figure 5C:
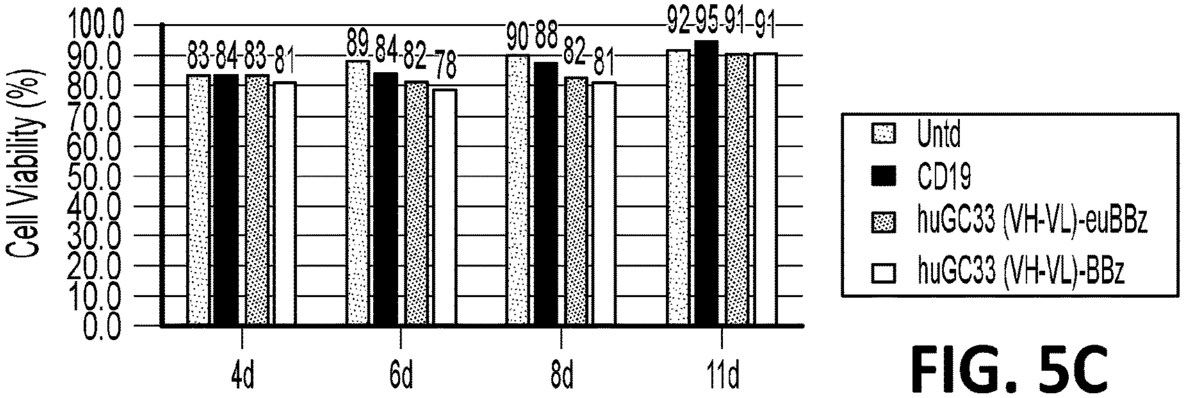
FIG. 5C is a graph showing cell viability of the CAR-T cells in vitro.

The cultured CAR-T cells were counted every 2-3 days, and fresh culture media and IL-2 was added after each counting (FIG. 5). On day 12, the cultured CAR-T cells were harvested and stored at −80° C. in a freezing container.

Figure 6:
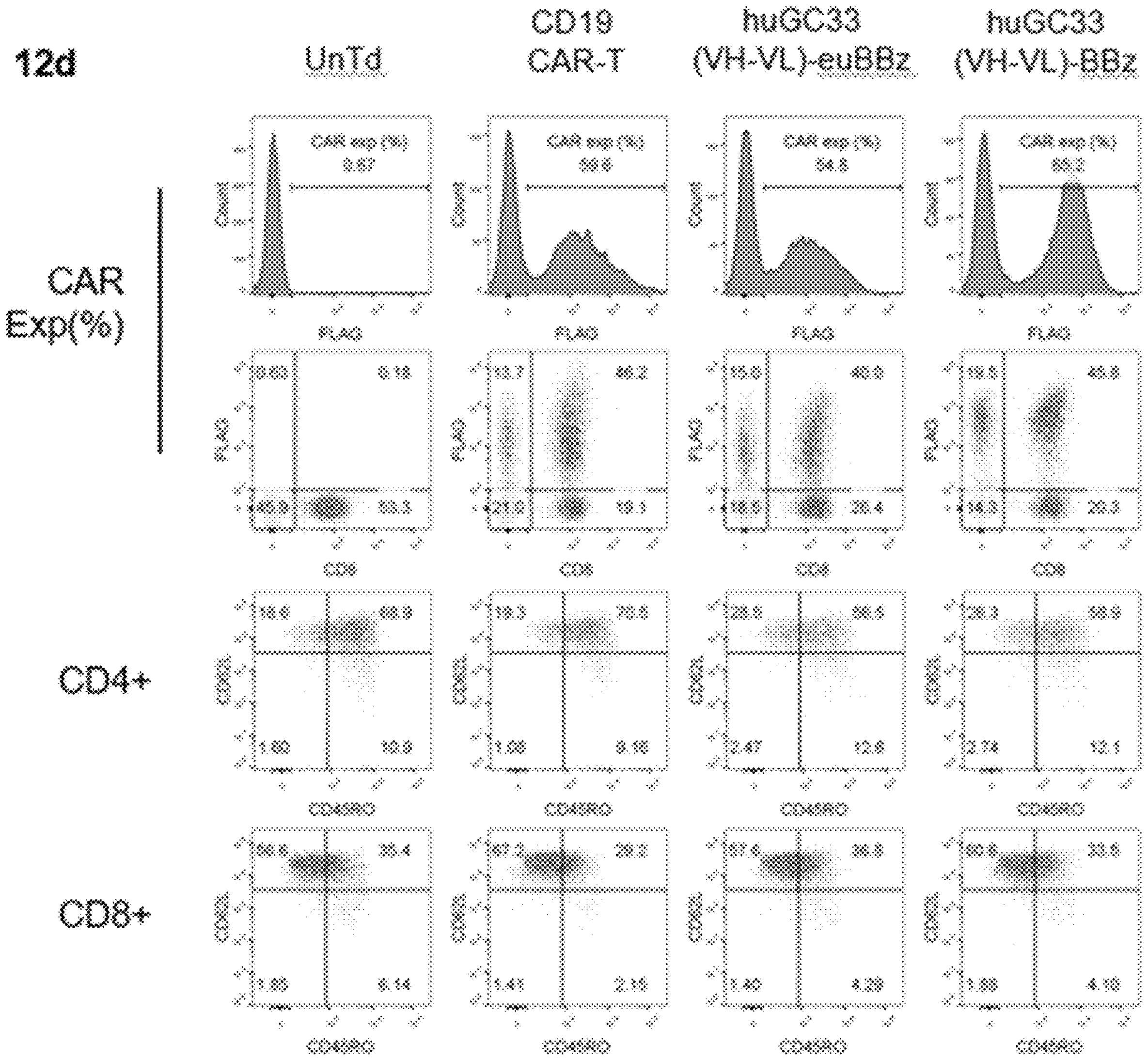
FIG. 6 shows analyses of T cells transduced with huGC33 (VH-VL)-euBBz and huGC33(VH-VL)-BBz for CAR expression.

CAR expression was analyzed on day 12 of culturing, and results show that the control group did not show expression while the CAR-T cell groups showed 54-66% CAR expression (FIG. 6).

Figure 7A:
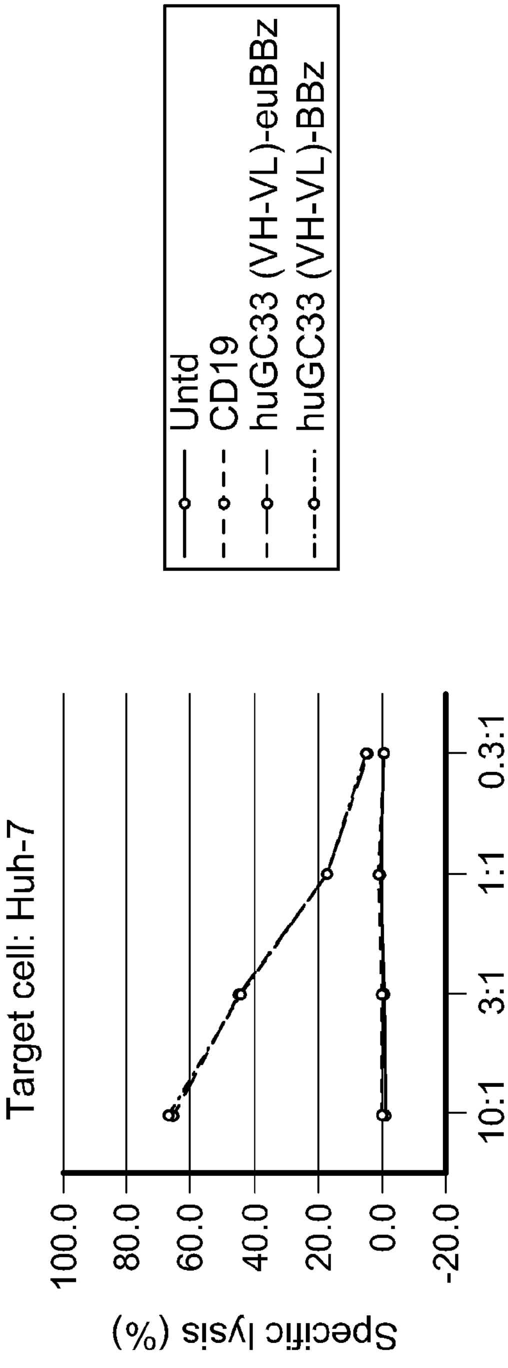
FIG. 7A is a graph showing LDH-based cytotoxicity assays with Target cells from Huh-7 cell line.
Figure 7B:
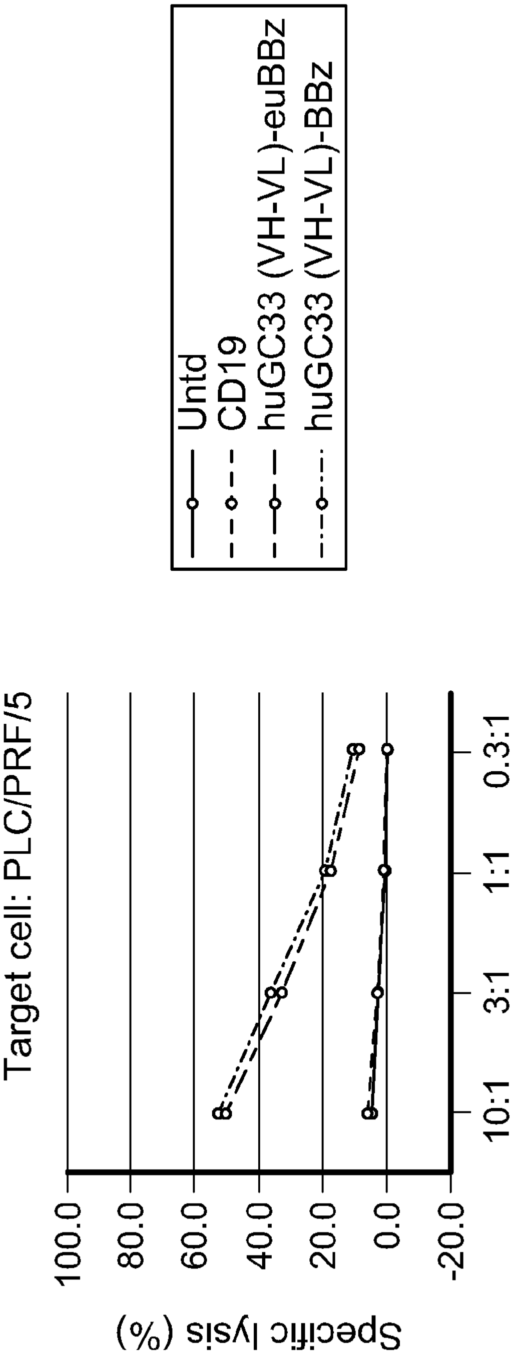
FIG. 7B is a graph showing LDH-based cytotoxicity assays with Target cells from PLC/PRF/5 cell line.

Target cells (GPC3 positive cell line) were harvested and seeded in a 96-well U bottom plate. Effector cells (CAR-T cells) were then added to the wells at Effector cell: Target cell ratios of 10:1, 3:1, 1:1, 0.3:1 and incubated for 24 hours at 37° C. After incubation, CytoTox96 Reagent was added to each well, and cytotoxicity was quantified by measuring absorbance at 490 nm (FIG. 7).

Figure 8:
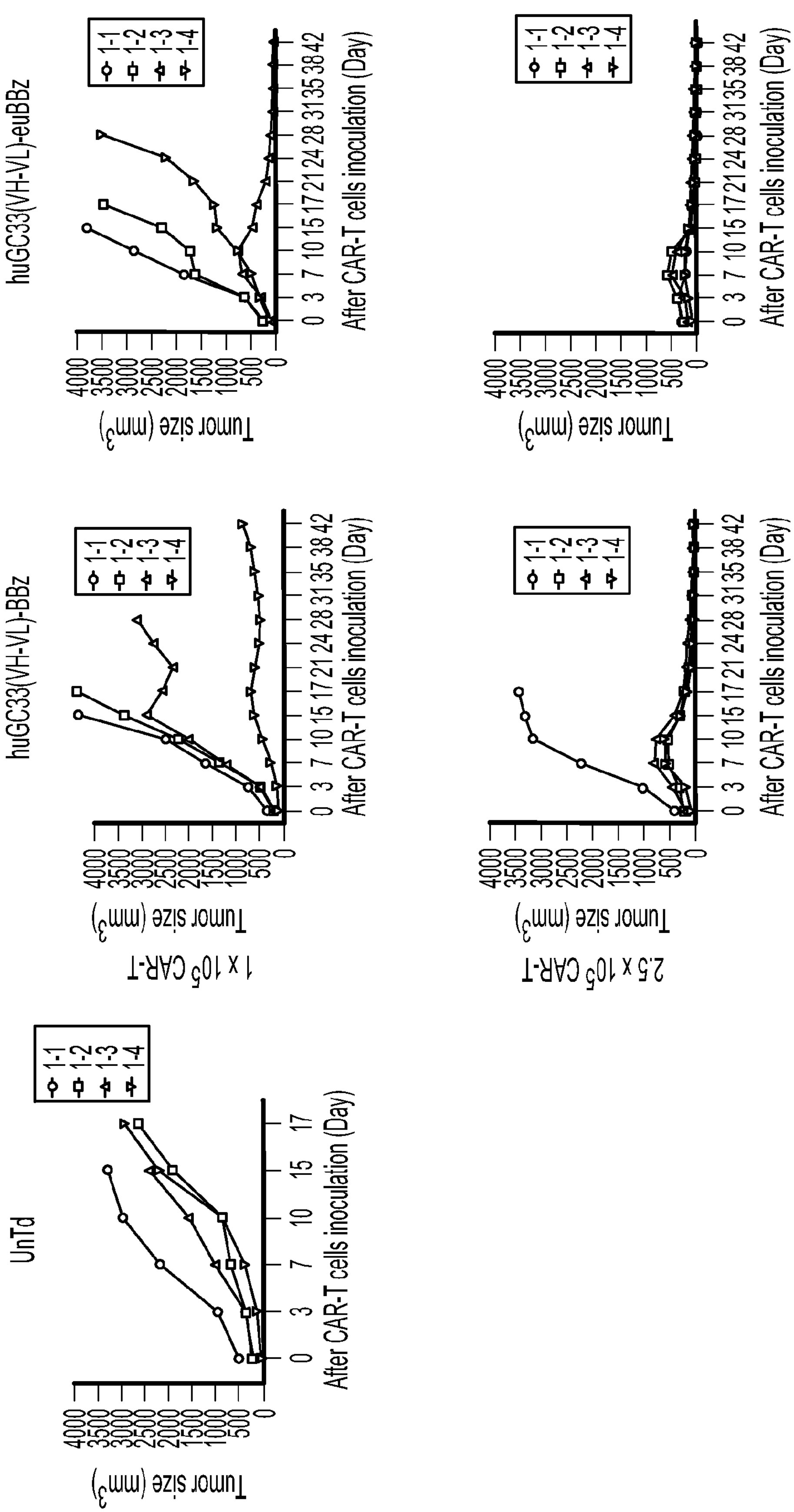
FIG. 8 is a set of graphs comparing in vivo efficacy of huGC33(VH-VL)-euBBz and huGC33(VH-VL)-BBz CAR-T cells.

Example 3—huGC33(VH-VL)-BBz CAR-T Cells and huGC33(VH-VL)-euBBz CAR-T Cells In Vivo In order to verify and compare the efficacy of huGC33 (VH-VL)-BBz CAR-T cells and huGC33(VH-VL)-euBBz CAR-T cells, Huh-7 Luf-GFP cells ($2\times10^6$ cells/200 μL/head) were injected into NSG mice (6-8 weeks old, male) and after 35 days post injection, the mice with a tumor size of about 200 $mm^3$ were separated into 5 groups, each group of 4 mice. The control group received injections of 5% HSA and other groups received injections with the CAR-T cells. Growth of the tumor was observed by measuring tumor size twice a week, using TM900 (FIG. 8).

Figure 9:
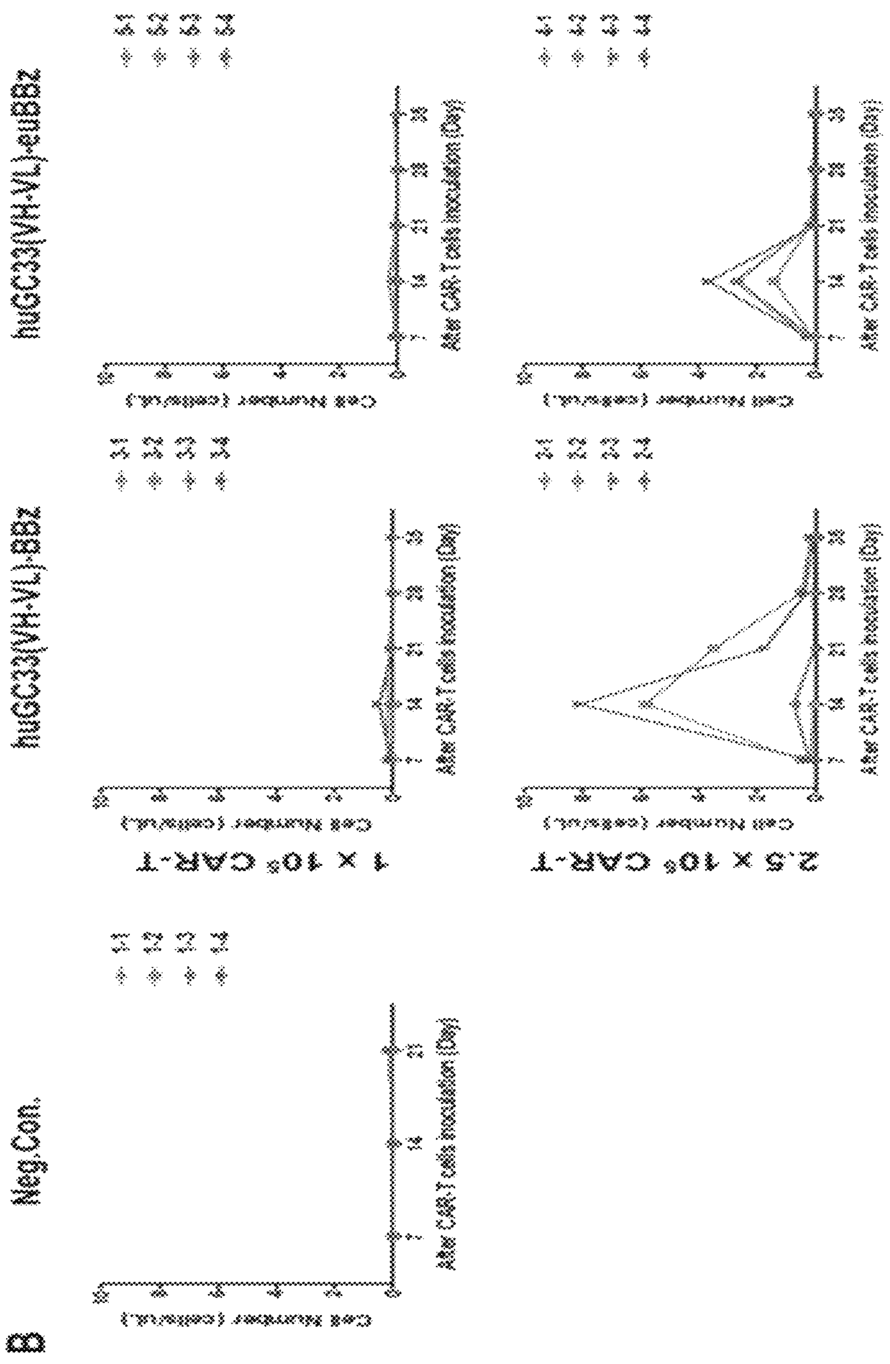
FIG. 9A is a graph showing the CAR-T cell count from the mouse model, 5 weeks post injection of huGC33(VH-VL)-euBBz and huGC33(VH-VL)-BBz CAR-T cells.
FIG. 9B is a set of graphs comparing the CAR-T cell count from the mouse model, 5 weeks post injection of huGC33(VH-VL)-euBBz and huGC33(VH-VL)-BBz CAR-T cells.

After CAR-T cell administration, orbital blood collection was performed from the mice once a week, wherein 100 μL of each blood sample was centrifuged at 12,000 rpm for 10 minutes to confirm the proportion of the CAR-T cells and the cell count. 100 μL of blood was placed in a FACS tube, and live/dead cell staining was performed using Zombie NIR™ Fixable Viability Kit. After reaching a concentration of 0.1 μL/100 μDPBS/tube, staining was performed at room temperature for 10 minutes. Counting beads 25 μL, CD45 0.5 μL, CD8 0.5 CD45RO 1.0 μL, CD62L 1.0 μL, PD-1 1.0 μL, Tim-3 1.0 μL, CD4 0.5 CD69 0.5 μL, and Flag 0.0125 μL were added to FACS buffer 100 μL and stained at room temperature for 30 minutes. After 30 minutes, 1×RBC lysis buffer was added and reacted at room temperature for 5 minutes. After centrifugation for 4 minutes at 2,000 rpm, all supernatant was discarded. 2 mL of FACS buffer was added to the tubes and centrifugation was performed for 4 minutes at 2,000 rpm, and analysis was performed using FACSCelesta (FIG. 9).

Figure 10:
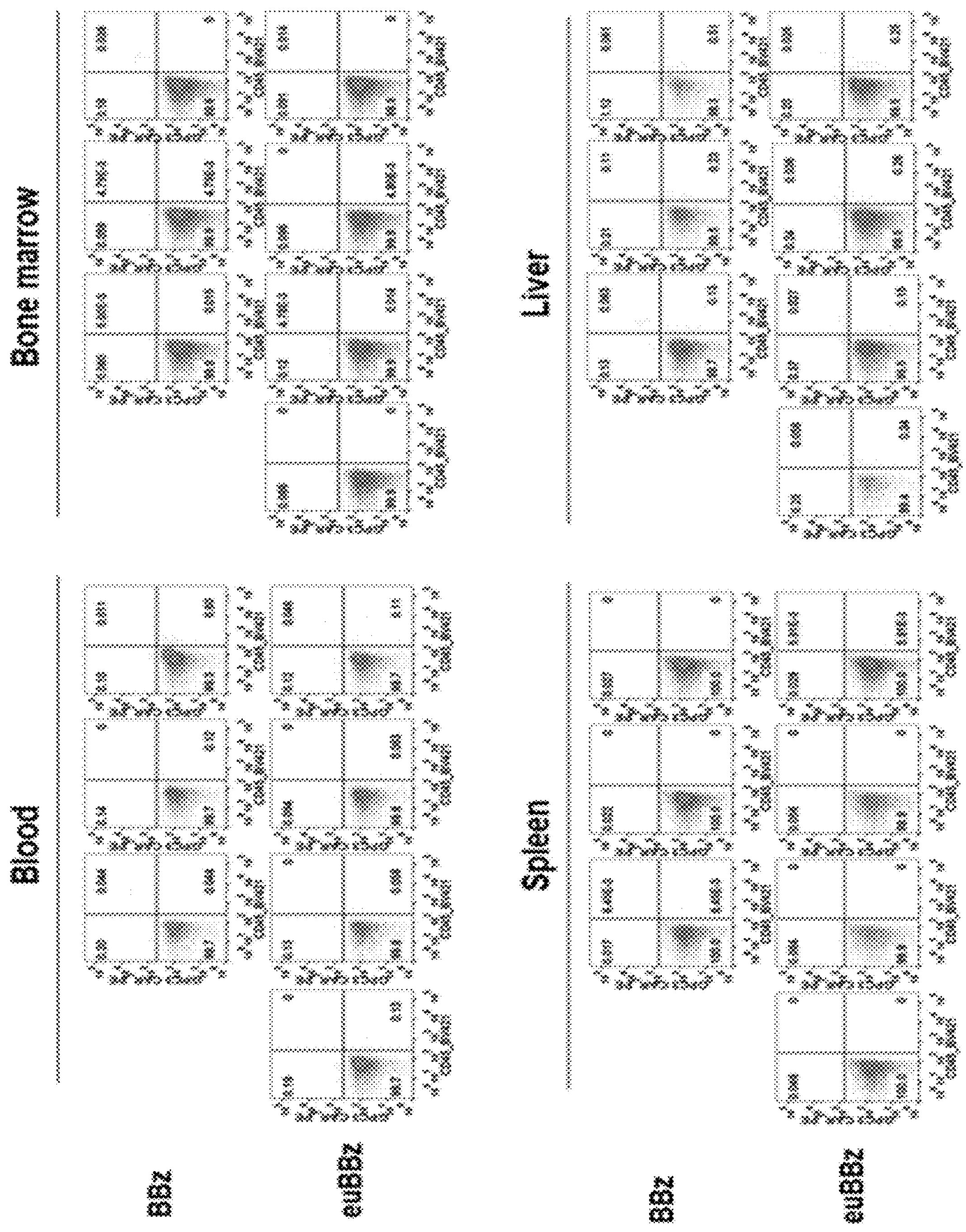
FIG. 10 show analyses of CAR-T cells in mouse blood, bone marrow, spleen, and liver, 5 weeks post injection of huGC33(VH-VL)-euBBz and huGC33(VH-VL)-BBz CAR-T cells using FACS staining.

After 6 weeks post injection of CAR-T injection, the mouse spleen, liver and bone marrow were harvested to evaluate the ratio of huGC33(VH-VL)-BBz CAR-T cells and huGC33(VH-VL)-euBBz CAR-T cells. Tissue samples were processed and filtered through a 40 cell strainer, then centrifuged at 2,000 rpm for 5 minutes and all supernatant was discarded. 5 μL 1×ACK buffer was added and reacted for 10 minutes. Then, 10 mL DPBS was added and centrifuged at 2,000 rpm for 5 minutes. FACS staining was performed as described above (FIG. 10).

Example 4—Construction of CD19-euBBz CAR

In order to increase immunological efficacy in the cytoplasmic signal domain 4-1BB, 5 amino acids were added in the 4-1BB cytoplasmic domain used in CAR-T, as a co-stimulatory signal factor, to newly construct a CAR expression vector (CD19-euBBz CAR). The completed construct comprises an anti-CD19, which is an scFv, including the EF1 alpha promoter, a hinge region and a transmembrane domain of human CD8, and an intracellular signaling domain. In particular, the intracellular signaling domain consists of a stimulatory domain and a co-stimulatory signaling domain. The intracellular signaling domain is 4-1BB, a co-stimulatory signal domain to which 5 consecutive amino acids were added, to which CD3 zeta was linked. The CAR gene fragment ultimately produced was conjugated to ELPS lentiviral expression vectors cleaved with BamH I and Sal I. In addition, cloning was performed using BamH I/Nhe I restriction enzyme to replace only the scFv part.

Example 5—CD19-euBBz and CD19-BBz CAR-T Cells

The 293T cell culture used for the production of recombinant lentiviruses contains medium comprising 10% FBS (Millipore, TMS-013-BKR) and 1×P/S (Gibco, 15140-122) in high glucose DMEM (Welgene, LM001-05). 293T cells were incubated in DMEM medium comprising 10% FBS for 24 hours prior to transduction in a 37° C. 5% CO2 incubator. The next day, for transfection, the transfection reagent and lentiviral plasmids were mixed at an appropriate proportion and incubated for 48 hours. The supernatant containing the lentivirus was then collected and centrifuged at 400×g for 10 minutes. In addition, the supernatant was filtered with a 0.45 μm syringe filter using a 50 mL syringe. The obtained supernatant was mixed 3:1 with a lentiviral enrichment kit (Clontech, 631231), and reacted at 4° C. for 24 to 48 hours. This was followed by centrifugation for 2 hours at 4° C. and 4,000 rpm to obtain a virus, which was resuspended in 0.5 mL RPMI (Welgene, LM001-01) not comprising FBS to produce a lentivirus.

To determine transduction efficiency of mammalian cells, Transformation Units (TU/mL) were measured by analyzing the particle count of the actual transduction-capable lentiviruses using Jurkat cells. CAR expression can be assayed by FACS. On the first day, Jurkat cells were seeded in 96-well plates at $1\times10^5$ cells/100 μL per well. On the second day, the lentivirus was serially diluted by ⅓ in 96-well plates, and the lentiviral transduction was performed on the already seeded Jurkat cells. At this time, by introducing polybrene (Millipore) into RPMI medium (10% FBS and 1×P/S), transduction of lentivirus was further increased. After centrifugation at 1200×g and 32° C. for 2 hours, the cells were incubated for 3 hours in a 37° C. 5% $CO_2$ incubator, and only 100 μL of RPMI only was added per well. On day 5, the flag of the lentivirus infected into the cell was stained with anti-Flag-DYKDDDDK (Biolegend, Cat No. 637310) to analyze the percentage of cells transduced with a flow cytometer. Using this, the titer was calculated as described in Follenzi and Naldini, 2002 (Follenzi and Naldini, 2002).

FACS staining was performed to confirm the production proportion of the two species of CAR-T cells after 14 days of incubation. For each CAR-T cell type, $2\times10^5$ cells were collected in FACS tubes (FALCON, Cat. No. 352052), and then 2 mL of FACS buffer was added and centrifugation was performed for 5 minutes at 2,000 rpm using a centrifuge (Thermo, ST16). After discarding the supernatant, 0.5 μL/tube anti-CD8 APC (SKI, Biolegend, Cat. No. 344722), 0.5 μL/tube anti-CD4 BV650 (RPA-T4, Biolegend, Cat. No. 300536) and 0.125 μL/tube anti-flag PE (L5, Biolegend, Cat. No. 637310) was added and staining was performed at room temperature for 30 minutes. After adding 2 mL of FACS buffer and centrifuging at 2,000 rpm for 5 minutes, this process was repeated one more time. For staining surviving/dead cells, 1 μL/tube 7-AAD (Biolegend, Cat. No. 420404) was added and the mixture was left for 5 minutes at room temperature and then analyzed using FACS (BD, FACSCelesta).

Figure 11:
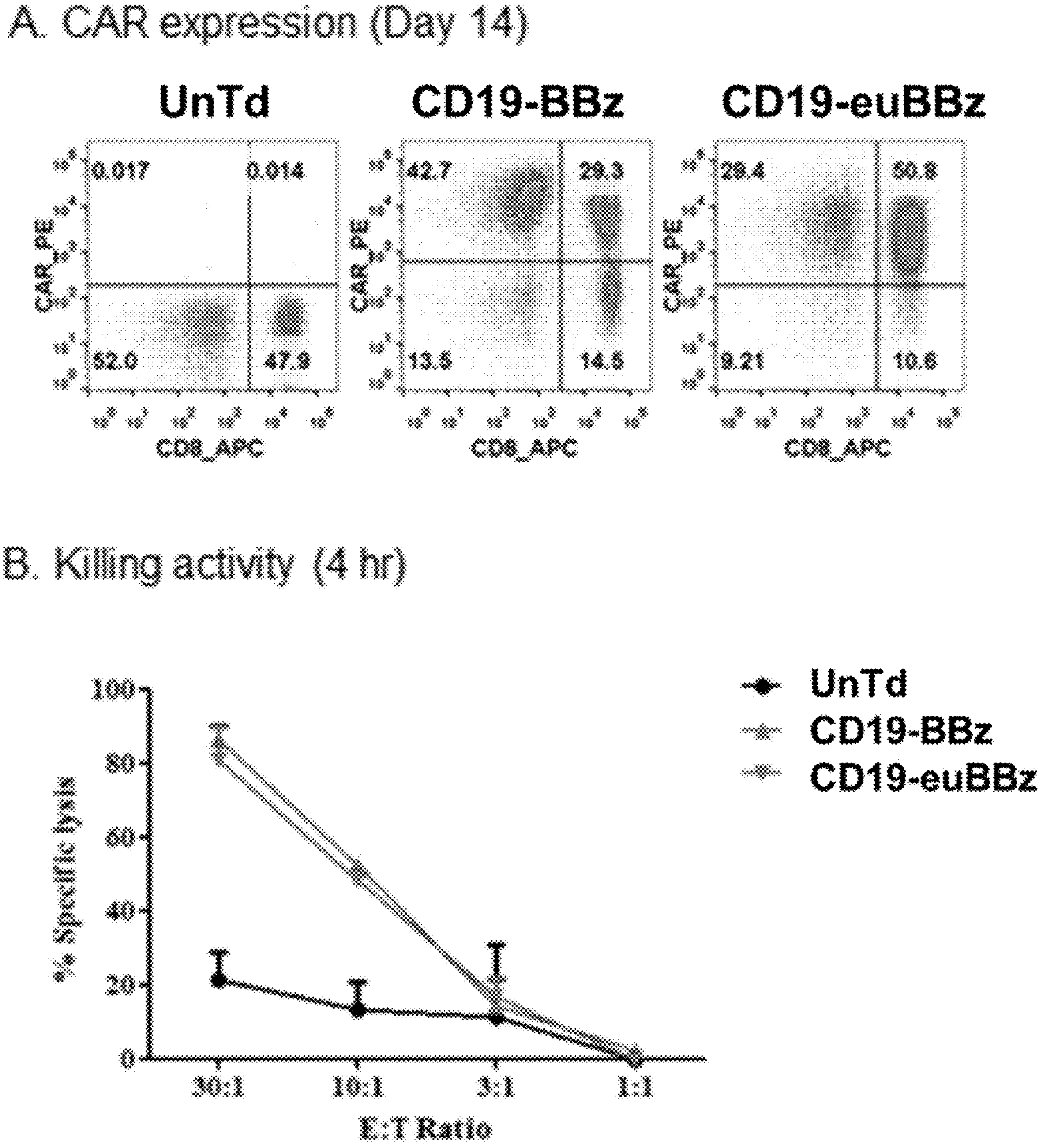
FIG. 11A shows CAR expression in T cells transduced with CD19-BBz and CD19-euBBz.
FIG. 11B is a graph from Luciferase-based cytotoxicity assay showing killing activity in T cells transduced with CD19-BBz and CD19-euBBz.

Confirmation of the proportion of the produced CD19 CAR-T cells using FACS staining confirmed that in the case of the improved-construct CD19-euBBZ CAR-T cells, the cell ratios were CD4+/CAR+ 29.4%, CD8+/CAR+ 50.8%, and total CAR-T 80.2%. It was confirmed that for the non-construct-improved CD19-BBz CAR-T cells, the cell ratios were 42.7% for CD4+/CAR+, 29.3% for CD8+/CAR+, and 72.0% for total CAR-T. Accordingly, it was confirmed that CD19-euBBz CAR-T cells had 8.2% higher expression of CAR than CD19-BBz CAR-T cells, and the CD8+/CAR+ cell was 21.5%, or about 2 times as many. (FIG. 11A)

Example 6—Confirmation of Cytotoxicity of Produced CD19 CAR-T Cells

To determine the cytotoxicity of the two CAR-T cell types cultured for 14 days, the CAR-T (E): LCL (T) proportion was brought to 30:1, 10:1, 3:1, and 1:1 in 96-well white plates (Corning, Cat. No. 3917). First, CAR-T cells were placed in wells at $6\times10^5$ cells/50 μL, $2\times10^5$ cells/50 μL, $9\times10^4$ cells/50 μL, and $2\times10^4$ cells/50 μL, respectively. Next, the target cell line, namely the CBK LCL-Luc cell line, was added to $2\times10^4$ cells/50 μL in a 37° C. $CO_2$ incubator (Mammert, INCO153med) and reacted for 4 hours. After 4 hours, 100 μL of Bright-Glo™ (Promega, Cat. No. E2620) was added to each well, and 5 minutes later, the relative light unit (RLU) value was measured using Luminometer (Thermo, Fluoroskan FL).

There was found to be no difference in cytotoxicity between CAR-T cells in which conventional 4-1BB was introduced and CAR-T cells in which euBBz containing five amino acids added to 4-1BB domain was introduced.

The results show, when two CAR-T cells and CBK LCL-Luc cell lines were incubated together at a proportion of 30:1, the cytotoxicity was found to be about 80% after 4 hours, and when they were incubated at 10:1, the cytotoxicity was about 50%. As the respective number of CAR-T cells incubated with cancer cells decreased by a factor of 3, the cytotoxicity decreased by about a factor of 3; in addition, when 5 amino acids were added to the 4-1BB domain in vitro, this was confirmed not to affect the in vitro cytotoxicity. (FIG. 11B)

Example 7—Induction of Subcutaneous Animal Models and Validation of CAR-T Through Automatic Caliper and IVIS Imaging For the experimental animals, NSG (NOD-scid IL2rγμL1) mice (The Jackson Laboratory) were used and managed under constant conditions in an animal nursery. The temperature was 23±2° C. with a 12 hour light/dark cycle and 50±10% humidity; feed and drink were provided ad libitum. In efficacy experiments using CD19-euBBz CAR-T with five amino acids added to the 4-1BB domain, CBK LCL-Luc cell lines were prepared at $2\times10^6$ cells/100 μL DPBS/head and injected subcutaneously in 6-week-old female mice to induce a subcutaneous animal model. When the cancer size reached between 50 and 100 $mm^3$ as measured using an automatic caliper (Youngbio, TM900), CD19-euBBz CAR-T cells and CD19-BBz CAR-T cells at $2\times10^6$ cells/100 μL DPBS/head (dose 1) and $6\times10^6$ cells/100 μL DPBS/head (dose 2) were administered once through the tail vein to confirm efficacy. In all animal experiments, cancer size and viability were confirmed periodically.

Figure 12:
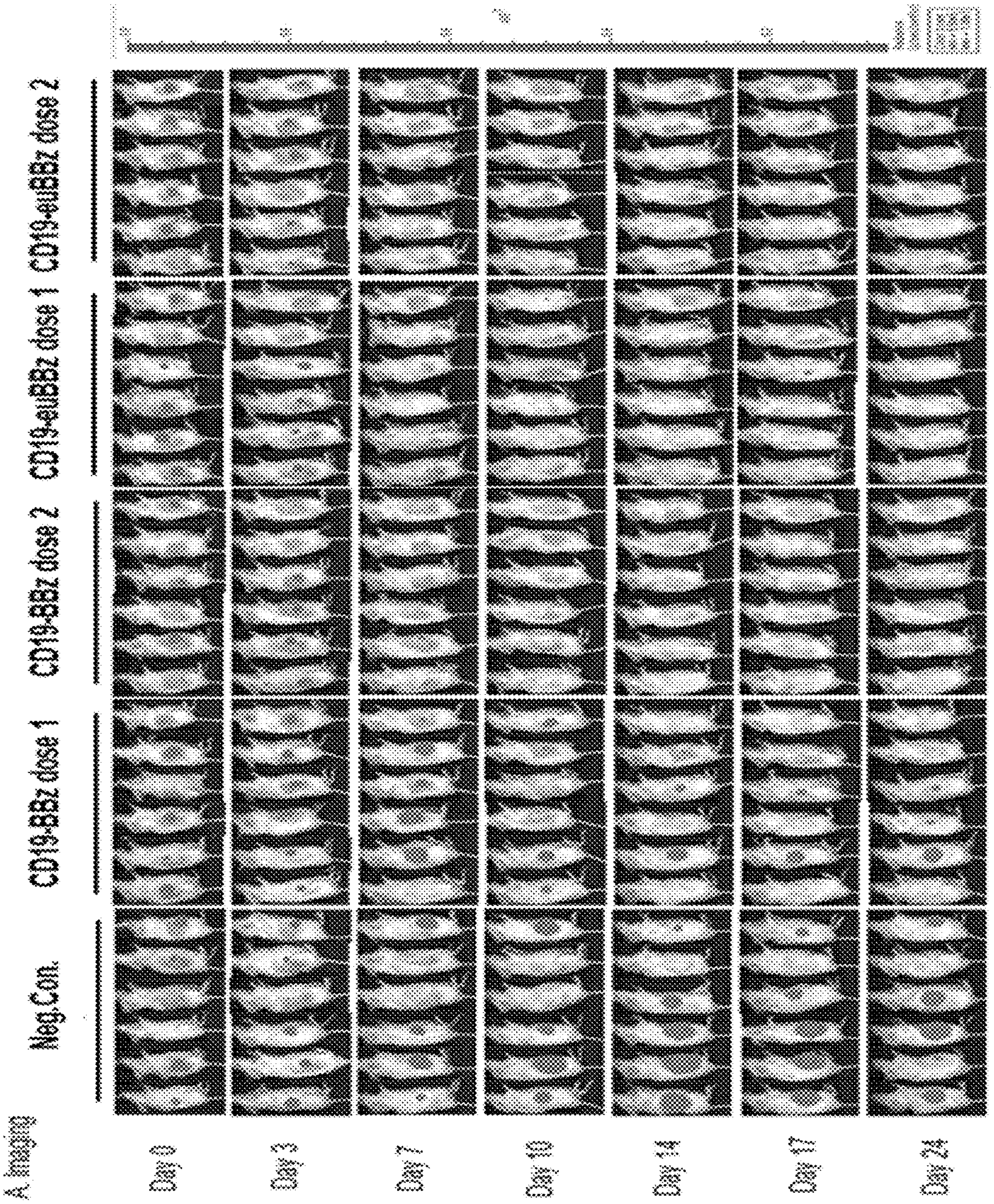
FIG. 12 shows results of IVIS imaging of the effects of CD19-BBz CAR-T and CD19-euBBz CAR-T cells using an animal model.
Figure 13:
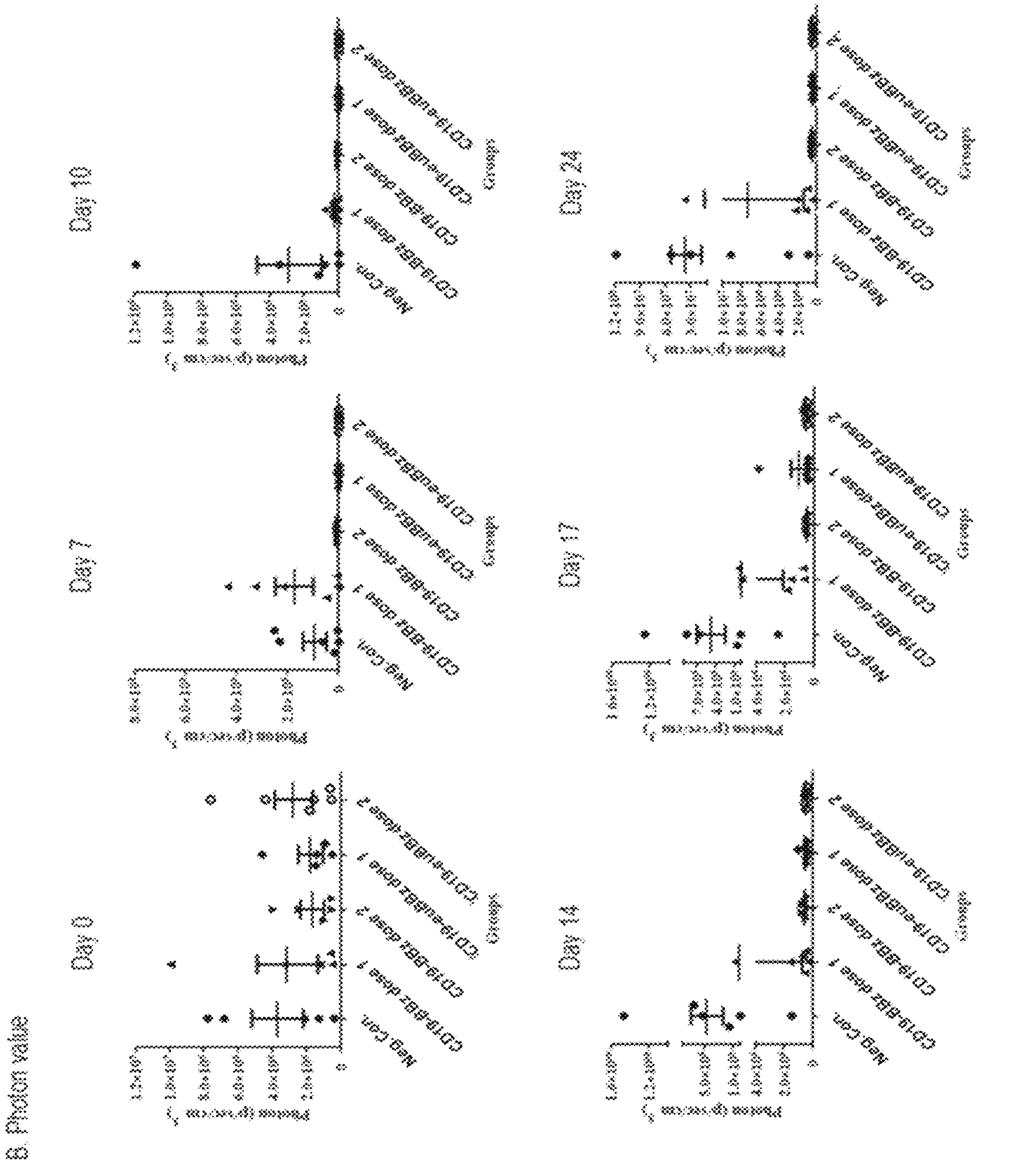
FIG. 13 are graphs showing photon values of the cancer cells in the animal model post injection of CD19-BBz CAR-T and CD19-euBBz CAR-T cells.

More specifically, cancer size and photon values were measured using automatic calipers and IVIS imaging equipment (PerkinElmer, Luna III), at 3 and 4-day intervals after CAR-T administration (FIG. 12, 13). In the case of using TM900, the cancer size was determined after placing the equipment at the cancer site. When confirming imaging and photon values using an IVIS imaging device, 150 mg/kg XenoLight™ D-luciferin (PerkinElmer, Cat. No. 122799) was first administered intraperitoneally in mice. After 15 minutes, inhalation anesthesia was induced using isoflurane, and 5 minutes later, IVIS was used for imaging the presence of cancer cells. After imaging, normalization was performed and the luciferase values (photon values) were then confirmed and graphed. After constructing a subcutaneous animal model using a CBK LCL-Luc cell line, the effects of CD19-BBz CAR-T and CD19-euBBz CAR-T cells were compared using IVIS imaging. As shown in FIG. 12, the effect could be confirmed within 1 week after administering the 2 species of CAR-T cells.

In the experimental group in which CD19-euBBz CAR-T cells was administered at $2\times10^6$ cells/100 μL DPBS/head and $6\times10^6$ cells/100 μL DPBS/head, cancer cells were observed on IVIS imaging 1 week after administration. In addition, in the group treated with CD19-BBz CAR-T, when $6\times10^6$ cells/100 μL DPBS/head was administered, cancer cells were rarely observed by imaging within 1 week of administration. However, cancer cells were identified in the experimental group administered CD19-BBz CAR-T after 1 week.

After 1 week after CAR-T administration, as shown in imaging, the value of luciferase imaged in each subject after the imaging process was determined; luciferase values were confirmed only in the group administered CD19 CAR-T at $2\times10^6$ cells/100 μL DPBS/head. When observed 3 weeks or more thereafter, the tumors continued to grow in mice not administered CAR-T cells, and no cancer cells were identified in the three experimental groups in which cancer cells disappeared initially. However, after 10 days, luciferase levels were decreased in the group receiving $2\times10^6$ cells/100 μL DPBS/head for CD19 CAR-T, but cancer cells did not disappear completely after 3 weeks. When administering the CD19-euBBz CAR-T $2\times10^6$ cells/100 μL DPBS/head, it was found via experimental imaging of cancer cells that the efficacy was similar to the group treated with CD19-BBz CAR-T at $6\times10^6$ cells/100 μL DPBS/head. The results showed that there was no difference in cytotoxicity of CD19-euBBz CAR-T and CD19-BBz CAR-T in vitro, but it was confirmed that the efficacy was 5 times better in CD19-euBBz CAR-T in animal models. (FIG. 12)

Example 8—Confirmation of Proportion of CD19-euBBz CAR-T in In Vivo Animal Model After CAR-T cell administration in a subcutaneous animal model to verify the potency of the improved-construct CAR-T cells, the presence of CAR-T was confirmed from mouse blood. More specifically, orbital blood collection was performed from mice at 3 and 4-day intervals after CAR-T administration. At a time of each blood collection, 70 μL of blood was collected and 60 μL of the blood was used to confirm the proportion of the CAR-T cells and the cell count. 60 μL blood was placed in a 5 mL FACS tube, and live/dead cell staining was performed using Zombie Aqua BV510 (Biolegend, Cat. No. 423101). After reaching a concentration of 0.1 μL/100 μL DPB S/tube, staining was performed at room temperature for 10 minutes. Since counting beads (Molecularprobes, Cat. No. C36950), anti-CD45 FITC (HI30, Biolegend, Cat. No. 304006), anti-CD8 BV786 (SK-1, Biolegend, Cat. No. 344740), anti-CD4 BV650 and anti-flag PE were added and stained at room temperature for 30 minutes. Each antibody was mixed in at 0.5 μL/100 μL FACS buffer/tube, and 25 μL of counting beads were added thereto. After 30 minutes 2 mL of ix RBC lysis buffer (Biolegend, Cat. No. 422401) was added and reacted at room temperature for 5 minutes. After centrifugation for 5 minutes at 2,000 rpm using a centrifuge, all supernatant was discarded. 2 mL of FACS wash buffer was added to this tube and centrifugation was performed for 5 min at 2,000 rpm. This process was repeated one more time, and then 50 μL of FACS buffer was added and analyzed using FACS.

Figure 14:
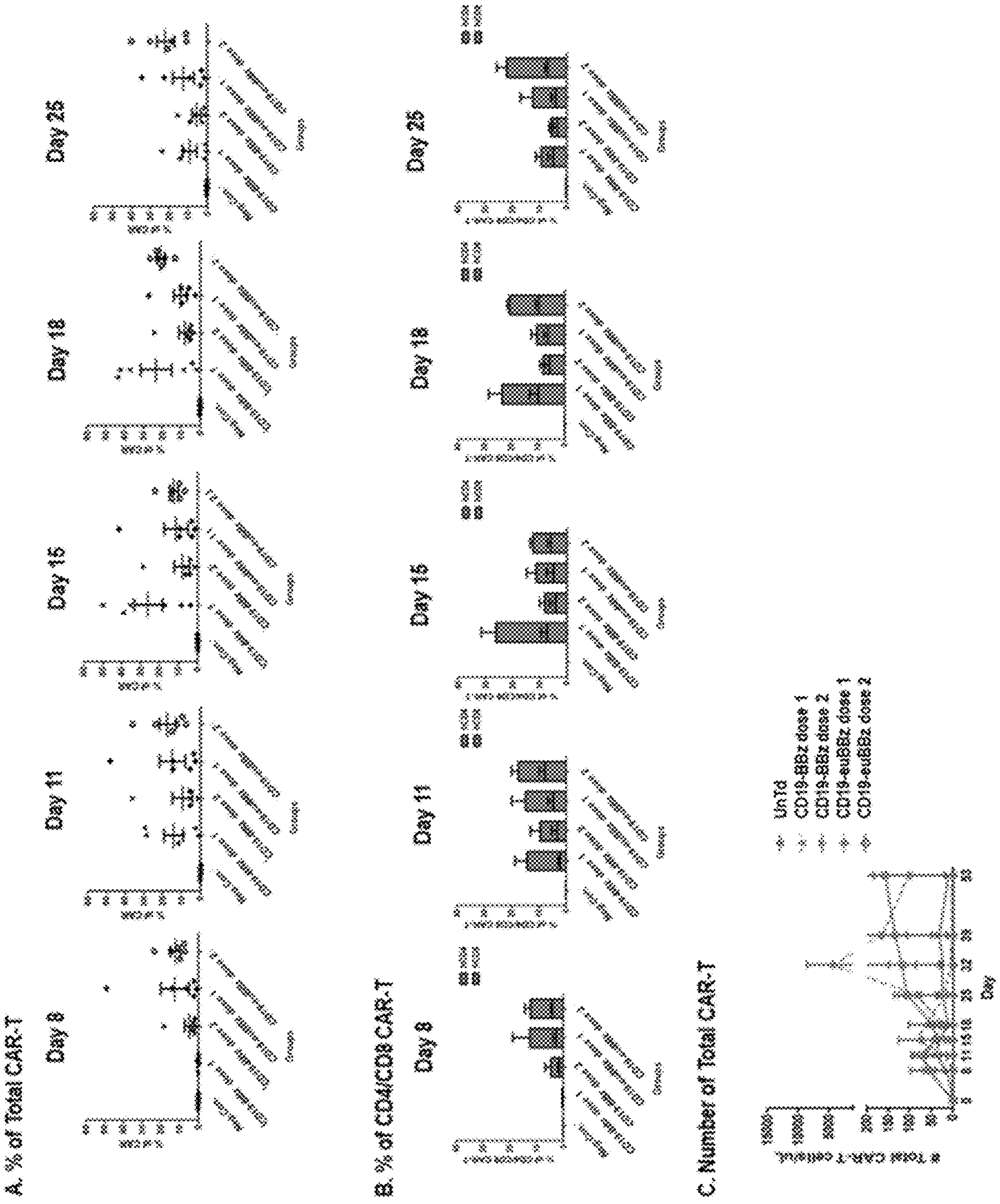
FIG. 14A is a set of graphs showing percentage of total CD19 CAR-T cells present in the blood using FACS after performing orbital blood collection in the mouse at 3-4 day intervals.
FIG. 14B is a set of graphs showing percentage of CD4/CD8 CAR-T cells present in the blood using FACS after performing orbital blood collection in the mouse at 3-4 day intervals.
FIG. 14C is a graph showing the number of total CD19 CAR-T present in the blood using FACS after performing orbital blood collection in the mouse at 3-4 day intervals.
Figure 15:
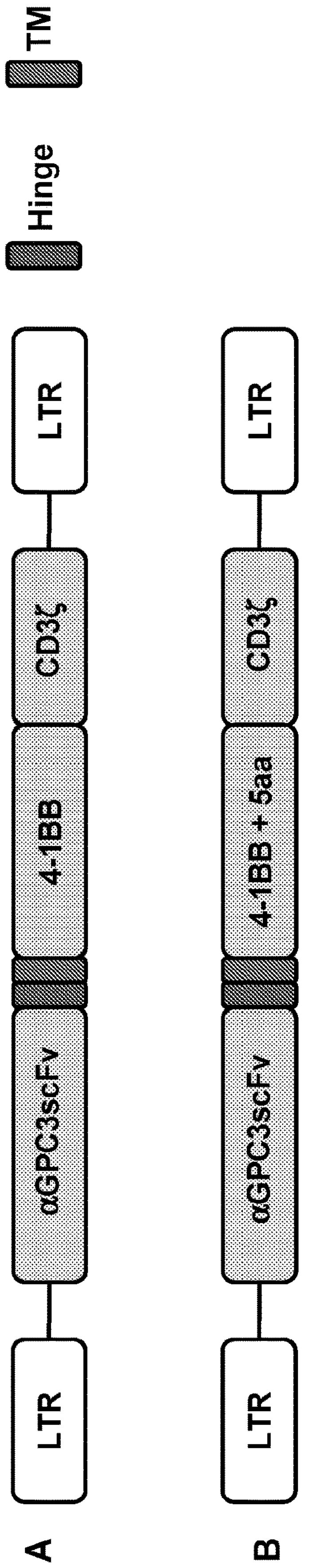
FIG. 15A shows a schematic of an exemplary GPC3 CAR construct.
FIG. 15B shows a schematic of an exemplary GPC3 CAR construct.

One week after CAR-T cell administration, in the CD19-euBBz CAR-T treatment group, approximately 20% CD19-euBBz CAR-T cells were confirmed in the blood in both the $2\times10^6$ cells/100 μL DPBS/head and $6\times10^6$ cells/100 μL DPBS/head groups; but in the CD19-BBz CAR-T-administered group, when $6\times10^6$ cells/100 μL DPBS/head was administered only 5% CD19 CAR-T was confirmed. 3 days later, the number and proportion of CAR-T cells in the mouse body reached a maximum and decreased. Within one week, in the 3 experimental groups in which CAR-T cells were identified (CD19-euBBz CAR-T; $2\times10^6$ cells/100 μL DPBS/head and $6\times10^6$ cells/100 μL DPBS/head, CD19-BBz CAR-T; $6\times10^6$ cells/100 μL DPBS/head), the cancer cells were killed quickly because it was possible for them to contact relatively many CAR-T cells before they proliferated in the mouse body. However, in the experimental group administered CD19-BBz CAR-T at $2\times10^6$ cells/100 μL DPBS/head, the proportion and number of CAR-T cells reached a maximum at 2 weeks, and the CAR-T proportion was about 25% with cancer cells proliferating relatively well. The CD19-euBBz CAR-T was more stable in quantity than the CD19-BBz CAR-T, after the CAR-T proportion initially increased and later decreased. In the case of CD19-BBz CAR-T, however, the proportion of CAR-T cells increased and decreased at a later time, and consequently it took longer for the tumor to disappear in the mouse body. As a result, as in the results of this experiment, the group administered CD19-euBBz CAR-T at $2\times10^6$ cells/100 μL DPBS/head exhibited similar CAR-T levels and effects in mice as the group administered CD19-BBz CAR-T at $6\times10^6$ cells/100 μL DPBS/head, indicating that CD19-euBBz CAR-T has a superior effect. (FIG. 14)

What is claimed is:

1. An immune cell comprising a chimeric antigen receptor (CAR), wherein the (CAR) comprises:

(a) an extracellular domain comprising an antigen-binding domain that specifically binds to glypican-3 (GPC3);

(b) a transmembrane domain; and (c) an intracellular domain comprising a costimulatory endodomain and an intracellular domain from CD3ζ, wherein the costimulatory endodomain comprises the amino acid sequence of SEQ ID NO: 4, and wherein the antigen-binding domain is an scFv, wherein the antigen-binding domain comprises a heavy-chain variable region consisting of an amino acid sequence of SEQ ID No: 16, and wherein the antigen-binding domain comprises a light-chain variable region consisting of an amino acid sequence of SEQ ID No: 15.

2. The immune cell of claim 1, wherein the chimeric antigen receptor is a single polypeptide.

3. The immune cell of claim 1, wherein the chimeric antigen receptor is comprised of two polypeptides.

4. The immune call of claim 1, wherein the costimulatory endodomain comprises the amino acid sequence encoded by the polynucleotide of SEQ ID NO: 2.

5. The immune cell of claim 1, wherein the antigen-binding domain is humanized.

6. The immune cell of claim 1, wherein the transmembrane domain is a transmembrane domain selected from a protein selected from the group consisting of: 4-1BB/CD137, an activating NK cell receptor, an immunoglobulin protein, B7-H3, BAFFR, BLAME (SLAMF8), BTLA, CD100 (SEMA4D), CD103, CD160 (BY55), CD 18, CD 19, CD 19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD 84, CD8, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), an integrin, ITGA4, ITGA6, ITGAD, ITGAE, ITGAL, ITGAM, ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1), an MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecule (a SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6.

7. The immune cell of claim 1, wherein the transmembrane domain is a transmembrane domain from CD8a.

8. The immune cell of claim 1, wherein the chimeric antigen receptor further comprises a signal peptide or leader sequence.

9. The immune cell of claim 1, wherein the chimeric antigen receptor further comprises a hinge region.

10. The immune cell of claim 9, wherein the hinge region is a CD8a hinge.

11. The immune cell of claim 1, wherein the chimeric antigen receptor further comprises an additional antigen-binding domain.

12. The immune cell of claim 11, wherein the additional antigen-binding domain is an scFv.

13. The immune cell of claim 1, wherein the immune cell is a human immune cell.

14. The immune cell of claim 1, wherein the immune cell is a T cell.

15. The immune cell of claim 1, wherein the immune cell is an NK cell.

16. A nucleic acid encoding a chimeric antigen receptor (CAR), wherein the chimeric antigen receptor comprises:

(a) an extracellular domain comprising an antigen-binding domain that specifically binds to glypican-3 (GPC3);

(b) a transmembrane domain; and (c) an intracellular domain comprising a costimulatory endodomain and an intracellular domain from CD3ζ, wherein the costimulatory endodomain comprises the amino acid sequence of SEQ ID NO: 4, and wherein the antigen-binding domain is an scFv, wherein the antigen-binding domain comprises a heavy-chain variable region consisting of an amino acid sequence of SEQ ID No: 16, and wherein the antigen-binding domain comprises a light-chain variable region consisting of an amino acid sequence of SEQ ID No: 15.

17. The nucleic acid of claim 16, wherein the chimeric antigen receptor is a single polypeptide.

18. The nucleic acid of claim 16, wherein the chimeric antigen receptor is comprised of two polypeptides.

19. The nucleic acid of claim 16, wherein the costimulatory endodomain comprises the amino acid sequence encoded by the polynucleotide of SEQ ID NO: 2.

20. The nucleic acid of claim 16, wherein the antigen-binding domain is humanized.

21. The nucleic acid of claim 16, wherein the transmembrane domain is a transmembrane domain selected from a protein selected from the group consisting of: 4-1BB/CD137, an activating NK cell receptor, an immunoglobulin protein, B7-H3, BAFFR, BLAME (SLAMF8), BTLA, CD100 (SEMA4D), CD103, CD160 (BY55), CD 18, CD 19, CD 19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD84, CD8, CD 8 alpha, CD 8 beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), an integrin, ITGA4, ITGA6, ITGAD, ITGAE, ITGAL, ITGAM, ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1), an MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecule (a SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6.

22. The nucleic acid of claim 16, wherein the transmembrane domain is a transmembrane domain from CD8 alpha.

23. The nucleic acid of claim 16, wherein the chimeric antigen receptor further comprises a signal peptide or leader sequence.

24. The nucleic acid of claim 16, wherein the chimeric antigen receptor further comprises a hinge region.

25. The nucleic acid of claim 24, wherein the hinge region is a CD8a hinge.

26. A vector comprising the nucleic acid of claim 16.

27. The vector of claim 26 further comprising a promoter operationally linked to the nucleic acid.

28. The vector of claim 27, wherein the promoter is a constitutive promoter.

29. The vector of claim 27, wherein the promoter is an inducible promoter.

30. The vector of claim 26, wherein the vector is a viral vector.

31. The vector of claim 30, wherein the viral vector is a lentiviral vector.

32. A method of producing an engineered immune cell, the method comprising: introducing into an immune cell the nucleic acid of claim 16 or a vector comprising the nucleic acid, thereby producing the engineered immune cell.

33. The method of claim 32, further comprising, after the introducing step, culturing the engineered immune cell.

34. The method of claim 32, wherein the immune cell is a T cell.

35. The method of claim 32, wherein the immune cell is a NK cell.

36. The method of claim 32, further comprising, before the introducing step, obtaining the immune cell from a subject.

37. The method of claim 36, wherein the method further comprises administering the engineered immune cell to the subject.

38. The method of claim 36, wherein the subject has been diagnosed or identified as having a cancer.

39. An engineered immune cell produced by the method of claim 32.

40. A pharmaceutical composition comprising the engineered immune cell of claim 39 and a pharmaceutically acceptable carrier.

41. A method of treating a glypican-3 expressing cancer in a subject, the method comprising administering to the subject an engineered immune cell of claim 39 or a pharmaceutical composition comprising the engineered immune cell.

42. The method of claim 41, wherein the cancer is carcinoma, lymphoma, blastoma, sarcoma, leukemia, squamous cell carcinoma, small cell lung cancer, non-small cell lung cancer, lung adenocarcinoma, squamous cell carcinoma of the lung, peritoneal cancer, hepatocellular carcinoma, gastric cancer, pancreatic cancer, glioma, cervical cancer, ovarian cancer, liver cancer, bladder cancer, breast cancer, colon cancer, colorectal cancer, endometrial or uterine carcinoma, salivary carcinoma, kidney cancer, prostate cancer, vulvar cancer, thyroid cancer, liver carcinoma, or head and neck cancer.

43. The method of claim 41, wherein the subject has previously been administered one or more additional anticancer therapies selected from the group consisting of: ionizing radiation, a chemotherapeutic agent, a therapeutic antibody, and a checkpoint inhibitor.

44. The method of claim 41, wherein the subject has been identified or diagnosed as having the cancer.

* * * * *

SEQUENCE LISTING

```
<160> NUMBER OF SEQ ID NOS: 28

<210> SEQ ID NO 1
<211> LENGTH: 15
<212> TYPE: DNA
<213> ORGANISM: Artificial
<220> FEATURE:
<223> OTHER INFORMATION: synthetic oligonucleotide

<400> SEQUENCE: 1

cgtttctctg ttgtt                                                   15


<210> SEQ ID NO 2
<211> LENGTH: 141
<212> TYPE: DNA
<213> ORGANISM: Artificial
<220> FEATURE:
<223> OTHER INFORMATION: synthetic oligonucleotide

<400> SEQUENCE: 2

cgtttctctg ttgttaaacg gggcagaaag aaactcctgt atatattcaa acaaccattt     60

atgagaccag tacaaactac tcaagaggaa gatggctgta gctgccgatt tccagaagaa    120

gaagaaggag gatgtgaact g                                              141


<210> SEQ ID NO 3
<211> LENGTH: 5
<212> TYPE: PRT
<213> ORGANISM: Artificial
<220> FEATURE:
<223> OTHER INFORMATION: synthetic polypeptide

<400> SEQUENCE: 3

Arg Phe Ser Val Val
1               5
```

<210> SEQ ID NO 4
<211> LENGTH: 47
<212> TYPE: PRT
<213> ORGANISM: Artificial
<220> FEATURE:
<223> OTHER INFORMATION: synthetic polyptpdie

<400> SEQUENCE: 4

Arg Phe Ser Val Val Lys Arg Gly Arg Lys Lys Leu Leu Tyr Ile Phe
1 5 10 15

Lys Gln Pro Phe Met Arg Pro Val Gln Thr Thr Gln Glu Glu Asp Gly
20 25 30

Cys Ser Cys Arg Phe Pro Glu Glu Glu Glu Gly Gly Cys Glu Leu
35 40 45

<210> SEQ ID NO 5
<211> LENGTH: 207
<212> TYPE: DNA
<213> ORGANISM: Artificial
<220> FEATURE:
<223> OTHER INFORMATION: CD8/Hinge/Transmembrane

<400> SEQUENCE: 5
accacgacgc cagcgccgcg accaccaaca ccggcgccca ccatcgctag ccagcccctg 60
tccctgcgcc cagaggcgtg ccggccagcg gcgggggcg cagtgcacac gagggggctg 120
gacttcgcct gtgatatcta catctgggcg cccttggccg ggacttgtgg ggtccttctc 180
ctgtcactgg ttatcaccct ttactgc 207

<210> SEQ ID NO 6
<211> LENGTH: 339
<212> TYPE: DNA
<213> ORGANISM: Artificial
<220> FEATURE:
<223> OTHER INFORMATION: synthetic oligonucleotide

<400> SEQUENCE: 6
agagtgaagt tcagcaggag cgcagacgcc cccgcgtaca agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgctaa 339

<210> SEQ ID NO 7
<211> LENGTH: 69
<212> TYPE: DNA
<213> ORGANISM: Artificial
<220> FEATURE:
<223> OTHER INFORMATION: CD8 alpha leader sequence

<400> SEQUENCE: 7
ggatccatgg ccttaccagt gaccgccttg ctcctgccgc tggccttgct gctccacgcc 60
gccaggccg 69

<210> SEQ ID NO 8
<211> LENGTH: 24
<212> TYPE: DNA
<213> ORGANISM: Artificial

<220> FEATURE:
<223> OTHER INFORMATION: Flag-tag sequence

<400> SEQUENCE: 8
gactacaagg acgacgatga caag 24

<210> SEQ ID NO 9
<211> LENGTH: 16
<212> TYPE: PRT
<213> ORGANISM: Artificial
<220> FEATURE:
<223> OTHER INFORMATION: Light chain CDR1

<400> SEQUENCE: 9

Arg Ser Ser Gln Ser Leu Val His Ser Asn Gly Asn Thr Tyr Leu His
1 5 10 15

<210> SEQ ID NO 10
<211> LENGTH: 7
<212> TYPE: PRT
<213> ORGANISM: Artificial
<220> FEATURE:
<223> OTHER INFORMATION: Light chain CDR2

<400> SEQUENCE: 10

Lys Val Ser Asn Arg Phe Ser
1 5

<210> SEQ ID NO 11
<211> LENGTH: 9
<212> TYPE: PRT
<213> ORGANISM: Artificial
<220> FEATURE:
<223> OTHER INFORMATION: Light chain CDR3

<400> SEQUENCE: 11

Ser Gln Asn Thr His Val Pro Pro Thr
1 5

<210> SEQ ID NO 12
<211> LENGTH: 5
<212> TYPE: PRT
<213> ORGANISM: Artificial
<220> FEATURE:
<223> OTHER INFORMATION: Heavy chain CDR1

<400> SEQUENCE: 12

Asp Tyr Glu Met His
1 5

<210> SEQ ID NO 13
<211> LENGTH: 17
<212> TYPE: PRT
<213> ORGANISM: Artificial
<220> FEATURE:
<223> OTHER INFORMATION: Heavy chain CDR2

<400> SEQUENCE: 13

Ala Leu Asp Pro Lys Thr Gly Asp Thr Ala Tyr Ser Gln Lys Phe Lys
1 5 10 15

Gly

<210> SEQ ID NO 14
<211> LENGTH: 6
<212> TYPE: PRT
<213> ORGANISM: Artificial

<220> FEATURE:
<223> OTHER INFORMATION: Heavy chain CDR3

<400> SEQUENCE: 14

Phe Tyr Ser Tyr Thr Tyr
1 5

<210> SEQ ID NO 15
<211> LENGTH: 112
<212> TYPE: PRT
<213> ORGANISM: Artificial
<220> FEATURE:
<223> OTHER INFORMATION: human GC33 light chain variable region

<400> SEQUENCE: 15

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val His Ser
20 25 30

Asn Gly Asn Thr Tyr Leu His Trp Tyr Gln Gln Arg Pro Gly Gln Ser
35 40 45

Pro Arg Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Asn
85 90 95

Thr His Val Pro Pro Thr Phe Gly Ser Gly Thr Lys Leu Glu Ile Lys
100 105 110

<210> SEQ ID NO 16
<211> LENGTH: 115
<212> TYPE: PRT
<213> ORGANISM: Artificial
<220> FEATURE:
<223> OTHER INFORMATION: human GC33 heavy chain variable region

<400> SEQUENCE: 16

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Glu Met His Trp Val Arg Gln Ala Pro Gly Gln Gly Leu Glu Trp Ile
35 40 45

Gly Ala Leu Asp Pro Lys Thr Gly Asp Thr Ala Tyr Ser Gln Lys Phe
50 55 60

Lys Gly Arg Ala Thr Leu Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Phe Tyr Ser Tyr Thr Tyr Trp Gly Gln Gly Thr Leu Val Thr
100 105 110

Val Ser Ser
115

<210> SEQ ID NO 17
<211> LENGTH: 336
<212> TYPE: DNA
<213> ORGANISM: Artificial
<220> FEATURE:

<223> OTHER INFORMATION: human GC33 light chain variable region

<400> SEQUENCE: 17

```
gacgtcgtta tgacacagag tcccctctcc ttgccggtga ccctgggtca gcctgcgtcc     60

atctcttgca gatcctccca gtctctggta cactccaacg gcaacacata cttgcactgg    120

taccaacaaa gacctggtca gtcaccgcga cttctcatat ataaagtttc caataggttc    180

agtggagtgc cagacaggtt cagtggttca ggatcaggca ctgatttcac gcttaaaatc    240

agtcgggttg aggcggagga cgtaggagtt tactattgca gccagaatac gcacgtgccg    300

cctacttttg gctctggaac caagttggaa ataaag                              336
```

<210> SEQ ID NO 18
<211> LENGTH: 345
<212> TYPE: DNA
<213> ORGANISM: Artificial
<220> FEATURE:
<223> OTHER INFORMATION: human GC33 heavy chain variable region

<400> SEQUENCE: 18

```
caagtgcaac tcgtacaatc aggtgctgaa gtcaaaaagc cgggagcctc tgttaaagtg     60

tcctgtaaag ccagcggcta cacctttacc gattatgaga tgcactgggt tcggcaggct    120

ccgggccaag gtctggagtg gatcggggct cttgacccaa agacgggcga cacggcttat    180

tcacaaaaat tcaaaggtag ggctactctg actgccgata agtccaccag caccgcgtat    240

atggagctct ctagcttgcg aagcgaggac acggcggtgt actattgcac acgcttctat    300

agttacacat attggggtca aggcacgctt gtgaccgtgt ctagc                    345
```

<210> SEQ ID NO 19
<211> LENGTH: 243
<212> TYPE: PRT
<213> ORGANISM: Artificial
<220> FEATURE:
<223> OTHER INFORMATION: synthetic polypeptide

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Phe Ser Leu Ser Arg Tyr Ser Val His Trp Ile Arg
145                 150                 155                 160

Gln Pro Pro Gly Lys Gly Leu Glu Trp Leu Gly Met Ile Trp Gly Gly
```

```
                165                 170                 175

Gly Ser Thr Asp Tyr Asn Ser Ala Leu Lys Ser Arg Leu Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Arg Asn Glu Gly Asp Thr
    210                 215                 220

Thr Ala Gly Thr Trp Phe Ala Tyr Trp Gly Gln Gly Thr Leu Val Thr
225                 230                 235                 240

Val Ser Ser
```

<210> SEQ ID NO 20
<211> LENGTH: 729
<212> TYPE: DNA
<213> ORGANISM: Artificial
<220> FEATURE:
<223> OTHER INFORMATION: synthetic oligonucleotide

<400> SEQUENCE: 20

```
gatattcaga tgacccagtc cccgagctcc ctgtccgcct ctgtgggcga tagggtcacc      60

atcacctgca aggccagtga ccacatcaac aactggctgg cctggtatca acagaaacca     120

ggaaaagctc cgaaactact gatcagcggc gccacctctc tggaaaccgg agtcccttct     180

cgcttctctg gttccggatc tgggaaggat tacactctga ccatcagcag tctgcagccg     240

gaagacttcg caacttatta ctgtcagcag tactggtcca ccccccttcac cttcggacag    300

ggtaccaagg tggagatcaa aggcggaggc ggatctggcg gcggaggaag tggcggaggg     360

ggatctcagg tgcagctgca ggagtcgggc ccaggactgg tgaagccttc ggagaccctg     420

tccctcacct gcactgtctc tggtttctcc ctgagtcggt actctgtgca ttggatccgg     480

cagcccccag ggaagggact ggagtggctg ggatgatct ggggaggcgg cagcaccgac      540

tacaacagcg ccctgaagtc ccgactgacc atatcaaagg acaactccaa gaaccaggtg     600

tccttgaagc tgagctctgt gaccgctgcg gacacggccg tgtattactg tgcgagaaat     660

gagggcgata ccaccgccgg cacttggttt gcctattggg gccagggaac cctggtcacc     720

gtctcctca                                                             729
```

<210> SEQ ID NO 21
<211> LENGTH: 242
<212> TYPE: PRT
<213> ORGANISM: Artificial
<220> FEATURE:
<223> OTHER INFORMATION: synthetic polypeptide

<400> SEQUENCE: 21

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95
```

```
Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser


<210> SEQ ID NO 22
<211> LENGTH: 726
<212> TYPE: DNA
<213> ORGANISM: Artificial
<220> FEATURE:
<223> OTHER INFORMATION: synthetic oligonucleotide

<400> SEQUENCE: 22

gacatccaga tgacacagac tacatcctcc ctgtctgcct ctctgggaga cagagtcacc      60

atcagttgca gggcaagtca ggacattagt aaatatttaa attggtatca gcagaaacca     120

gatggaactg ttaaactcct gatctaccat acatcaagat tacactcagg agtcccatca     180

aggttcagtg gcagtgggtc tggaacagat tattctctca ccattagcaa cctggagcaa     240

gaagatattg ccacttactt ttgccaacag ggtaatacgc ttccgtacac gttcggaggg     300

gggaccaagc tggagatcac aggtggcggt ggctcgggcg gtggtgggtc gggtggcggc     360

ggatctgagg tgaaactgca ggagtcagga cctggcctgg tggcgccctc acagagcctg     420

tccgtcacat gcactgtctc aggggtctca ttacccgact atggtgtaag ctggattcgc     480

cagcctccac gaaagggtct ggagtggctg ggagtaatat ggggtagtga aaccacatac     540

tataattcag ctctcaaatc cagactgacc atcatcaagg acaactccaa gagccaagtt     600

ttcttaaaaa tgaacagtct gcaaactgat gacacagcca tttactactg tgccaaacat     660

tattactacg gtggtagcta tgctatggac tactggggcc aaggaacctc agtcaccgtc     720

tcctca                                                                726


<210> SEQ ID NO 23
<211> LENGTH: 1184
<212> TYPE: DNA
<213> ORGANISM: Artificial
<220> FEATURE:
<223> OTHER INFORMATION: synthetic oligonucleotide

<400> SEQUENCE: 23

cgtgaggctc cggtgcccgt cagtgggcag agcgcacatc gcccacagtc cccgagaagt      60

tggggggagg ggtcggcaat tgaaccggtg cctagagaag gtggcgcggg gtaaactggg     120
```

aaagtgatgt cgtgtactgg ctccgccttt ttcccgaggg tgggggagaa ccgtatataa 180
gtgcagtagt cgccgtgaac gttctttttc gcaacgggtt tgccgccaga acacaggtaa 240
gtgccgtgtg tggttcccgc gggcctggcc tctttacggg ttatggccct tgcgtgcctt 300
gaattacttc cacctggctg cagtacgtga ttcttgatcc cgagcttcgg gttggaagtg 360
ggtgggagag ttcgaggcct tgcgcttaag gagccccttc gcctcgtgct tgagttgagg 420
cctggcctgg gcgctggggc cgccgcgtgc gaatctggtg gcaccttcgc gcctgtctcg 480
ctgctttcga taagtctcta gccatttaaa atttttgatg acctgctgcg acgctttttt 540
tctggcaaga tagtcttgta aatgcgggcc aagatctgca cactggtatt tcggtttttg 600
gggccgcggg cggcgacggg gcccgtgcgt cccagcgcac atgttcggcg aggcggggcc 660
tgcgagcgcg gccaccgaga atcggacggg ggtagtctca agctggccgg cctgctctgg 720
tgcctggcct cgcgccgccg tgtatcgccc cgccctgggc ggcaaggctg gcccggtcgg 780
caccagttgc gtgagcggaa agatggccgc ttcccggccc tgctgcaggg agctcaaaat 840
ggaggacgcg gcgctcggga gagcgggcgg gtgagtcacc cacacaaagg aaaagggcct 900
ttccgtcctc agccgtcgct tcatgtgact ccactgagta ccgggcgccg tccaggcacc 960
tcgattagtt ctcgagcttt tggagtacgt cgtctttagg ttggggggag gggttttatg 1020
cgatggagtt tccccacact gagtgggtgg agactgaagt taggccagct tggcacttga 1080
tgtaattctc cttggaattt gcccttttg agtttggatc ttggttcatt ctcaagcctc 1140
agacagtggt tcaaagtttt tttcttccat ttcaggtgtc gtga 1184

<210> SEQ ID NO 24
<211> LENGTH: 84
<212> TYPE: DNA
<213> ORGANISM: Artificial
<220> FEATURE:
<223> OTHER INFORMATION: synthetic oligonucleotide

<400> SEQUENCE: 24
agtagtgtgt gcccgtctgt tgtgtgactc tggtaactag agatccctca gaccctttta 60
gtcagtgtgg aaaatctcta gcag 84

<210> SEQ ID NO 25
<211> LENGTH: 1377
<212> TYPE: DNA
<213> ORGANISM: Artificial
<220> FEATURE:
<223> OTHER INFORMATION: synthetic oligonucleotide

<400> SEQUENCE: 25
cgaacaggga cttgaaagcg aaagggaaac cagaggagct ctctcgacgc aggactcggc 60
ttgctgaagc gcgcacggca agaggcgagg ggcggcgact ggtgagtacg ccaaaaattt 120
tgactagcgg aggctagaag gagagagatg ggtgcgagag cgtcagtatt aagcggggga 180
gaattagatc gcgatgggaa aaaattcggt taaggccagg gggaaagaaa aaatataaat 240
taaaacatat agtatgggca agcagggagc tagaacgatt cgcagttaat cctggcctgt 300
tagaaacatc agaaggctgt agacaaatac tgggacagct acaaccatcc cttcagacag 360
gatcagaaga acttagatca ttatataata cagtagcaac cctctattgt gtgcatcaaa 420
ggatagagat aaaagacacc aaggaagctt tagacaagat agaggaagag caaaacaaaa 480
gtaagaccac cgcacagcaa gcggccgctg atcttcagac ctggaggagg agatatgagg 540
gacaattgga gaagtgaatt atataaatat aaagtagtaa aaattgaacc attaggagta 600
gcacccacca aggcaaagag aagagtggtg cagagagaaa aaagagcagt gggaatagga 660
gctttgttcc ttgggttctt gggagcagca ggaagcacta tgggcgcagc gtcaatgacg 720
ctgacggtac aggccagaca attattgtct ggtatagtgc agcagcagaa caatttgctg 780
agggctattg aggcgcaaca gcatctgttg caactcacag tctggggcat caagcagctc 840
caggcaagaa tcctggctgt ggaaagatac ctaaaggatc aacagctcct ggggatttgg 900
ggttgctctg gaaaactcat ttgcaccact gctgtgcctt ggaatgctag ttggagtaat 960
aaatctctgg aacagatttg gaatcacacg acctggatgg agtgggacag agaaattaac 1020
aattacacaa gcttaataca ctccttaatt gaagaatcgc aaaaccagca agaaaagaat 1080
gaacaagaat tattggaatt agataaatgg gcaagtttgt ggaattggtt taacataaca 1140
aattggctgt ggtatataaa attattcata atgatagtag gaggcttggt aggtttaaga 1200
atagtttttg ctgtactttc tatagtgaat agagttaggc agggatattc accattatcg 1260
tttcagaccc acctcccaac cccgagggga cccgacaggc ccgaaggaat agaagaagaa 1320
ggtggagaga gagacagaga cagatccatt cgattagtga acggatctcg acggtat 1377

<210> SEQ ID NO 26
<211> LENGTH: 547
<212> TYPE: DNA
<213> ORGANISM: Artificial
<220> FEATURE:
<223> OTHER INFORMATION: synthetic oligonucleotide

<400> SEQUENCE: 26
tagactgtag cccaggaata tggcagctag attgtacaca tttagaagga aaagttatct 60
tggtagcagt tcatgtagcc agtggatata tagaagcaga agtaattcca gcagagacag 120
ggcaagaaac agcatacttc ctcttaaaat tagcaggaag atggccagta aaaacagtac 180
atacagacaa tggcagcaat ttcaccagta ctacagttaa ggccgcctgt tggtgggcgg 240
ggatcaagca ggaatttggc attccctaca atccccaaag tcaaggagta atagaatcta 300
tgaataaaga attaaagaaa attataggac aggtaagaga tcaggctgaa catcttaaga 360
cagcagtaca aatggcagta ttcatccaca attttaaaag aaaagggggg attgggggt 420 acagtgcagg ggaaagaata gtagacataa tagcaacaga catacaaact aaagaattac 480
aaaaacaaat tacaaaaatt caaaattttc gggtttatta cagggacagc agagatccag 540
tttggct 547

<210> SEQ ID NO 27
<211> LENGTH: 591
<212> TYPE: DNA
<213> ORGANISM: Artificial
<220> FEATURE:
<223> OTHER INFORMATION: synthetic oligonucleotide

<400> SEQUENCE: 27
atcaacctct ggattacaaa atttgtgaaa gattgactgg tattcttaac tatgttgctc 60
cttttacgct atgtggatac gctgctttaa tgcctttgta tcatgctatt gcttcccgta 120
tggctttcat tttctcctcc ttgtataaat cctggttgct gtctctttat gaggagttgt 180
ggcccgttgt caggcaacgt ggcgtggtgt gcactgtgtt tgctgacgca acccccactg 240
gttggggcat tgccaccacc tgtcagctcc tttccgggac tttcgctttc cccctcccta 300
ttgccacggc ggaactcatc gccgcctgcc ttgcccgctg ctggacaggg gctcggctgt 360

-continued

```
tgggcactga caattccgtg gtgttgtcgg ggaagctgac gtcctttcca tggctgctcg    420

cctgtgttgc cacctggatt ctgcgcggga cgtccttctg ctacgtccct tcggccctca    480

atccagcgga ccttccttcc cgcggcctgc tgccggctct gcggcctctt ccgcgtcttc    540

gccttcgccc tcagacgagt cggatctccc tttgggccgc ctccccgcct g             591


<210> SEQ ID NO 28
<211> LENGTH: 98
<212> TYPE: DNA
<213> ORGANISM: Artificial
<220> FEATURE:
<223> OTHER INFORMATION: synthetic oligonucleotide

<400> SEQUENCE: 28

gggtctctct ggttagacca gatctgagcc tgggagctct ctggctaact agggaaccca     60

ctgcttaagc ctcaataaag cttgccttga gtgcttca                             98
```